(12) United States Patent
Cohen

(10) Patent No.: US 12,210,021 B2
(45) Date of Patent: Jan. 28, 2025

(54) METHODS FOR DIAGNOSING FERTILITY OF EJACULATES FOR ARTIFICIAL INSEMINATION

(71) Applicant: AREX LIFE SCIENCES, LLC, Watertown, MA (US)

(72) Inventor: Barb A. Cohen, Watertown, MA (US)

(73) Assignee: AREX LIFE SCIENCES, LLC, Watertown, MA (US)

( * ) Notice: Subject to any disclaimer, the term of this patent is extended or adjusted under 35 U.S.C. 154(b) by 1004 days.

(21) Appl. No.: 17/059,946

(22) PCT Filed: May 30, 2019

(86) PCT No.: PCT/US2019/034601
§ 371 (c)(1),
(2) Date: Nov. 30, 2020

(87) PCT Pub. No.: WO2019/232178
PCT Pub. Date: Dec. 5, 2019

(65) Prior Publication Data
US 2021/0208154 A1 Jul. 8, 2021

Related U.S. Application Data

(60) Provisional application No. 62/678,205, filed on May 30, 2018.

(51) Int. Cl.
*G01N 33/68* (2006.01)
*A01N 1/02* (2006.01)
(Continued)

(52) U.S. Cl.
CPC ......... *G01N 33/689* (2013.01); *A01N 1/0284* (2013.01); *A61B 17/43* (2013.01);
(Continued)

(58) Field of Classification Search
CPC .... G01N 33/689; A01N 1/0284; A61B 17/43; A61B 2503/40; A61D 19/02; C12N 5/061; C12N 2501/01; C12N 2501/999
See application file for complete search history.

(56) References Cited

U.S. PATENT DOCUMENTS 5,219,729 A 6/1993 Hodgen
5,779,363 A 7/1998 Freire et al.
(Continued)

FOREIGN PATENT DOCUMENTS

JP 2016519290 A 6/2016
WO 2011041524 A1 4/2011
(Continued)

OTHER PUBLICATIONS

International Preliminary Report on Patentability for PCT/US2019/034601 dated Dec. 1, 2020.
(Continued)

*Primary Examiner* — Samuel G Gilbert
(74) *Attorney, Agent, or Firm* — Bryan D. Zerhusen, Esq.; Nicholas R. Herrel, Esq.; CANTOR COLBURN LLP

(57) ABSTRACT

In accord with the present invention, the fertility quality of an ejaculate can be determined by assaying sperm, in aliquots of the ejaculate or of an ejaculate produced previously by the same male, at intervals over a period of time. Fertility quality is determined by the number of times the level of expression of a marker on the sperm goes through a maximum level of expression during the period of time and if desired by sperm state and fertilization procedure used. The marker should be capable of correlation with the level of Fc receptor (FcR) expression on the sperm. The fertility quality of the ejaculate is related to the number of times a maximum level of expression is reached.

16 Claims, 18 Drawing Sheets

(51) Int. Cl.
*A61B 17/43* (2006.01)
*A61D 19/02* (2006.01)
*C12N 5/076* (2010.01)

(52) U.S. Cl.
CPC ............. *A61D 19/02* (2013.01); *C12N 5/061* (2013.01); *A61B 2503/40* (2013.01); *C12N 2501/01* (2013.01); *C12N 2501/999* (2013.01)

(56) References Cited

U.S. PATENT DOCUMENTS

2012/0209138 A1    8/2012   Kirsner
2012/0252000 A1*  10/2012   Cohen ................ G01N 33/5091
                                                              435/2

FOREIGN PATENT DOCUMENTS

WO           2014150480 A1    9/2014
WO       WO 2018/132838 A2    7/2018

OTHER PUBLICATIONS

Agarwal, A., et al., "A unique view on male infertility around the globe." Reprod. Biol. Endocrinol. 13: 37. DOI 10.1186/s12958-015-0032-1 (Apr. 25, 2015).

Ahlgren, M., et al., "Sperm transport and survival in women with special reference to the Fallopian tube", The Biology of Spermatozoa INSERM Int. Symp., Nouzilly 1973, pp. 63-73 (eds. Hafez, E.S.E., and Thibault, C.G.) (Karger, Basel 1975).

Alukal, J.P., et al., "Safety of assisted reproduction, assessed by risk of abnormalities in children born after use of in vitro fertilization techniques", Nature Clin. Practice 5(3): 140-150 (Feb. 5, 2008).

Barratt, C., et al., "Diagnostic tools in male infertility—the question of sperm dysfunction." Asian Journal of Andrology, 13: 53-58 (Nov. 10, 2010).

Bearer, E.L., et al., Morphology of Mammalian Sperm Membranes During Differentiation, Maturation, and Capacitation, J Elecon Micros Tech. 16: 281-297 (Dec. 1990).

Cohen-Dayag, A., et al., Sperm capacitation in humans is transient and correlates with chemotactic responsiveness to follicular factors. Proc. Natl. Acad. Sci. 92: 11039-11043 (Nov. 1995).

Fischer, B., et al., "Oxygen tension in the oviduct and uterus of rhesus monkeys, hamsters and rabbits", J. Reprod. and Fert. (1993) 99: 673-679.

Guthrie, H.D., et al., "Effects of reactive oxygen species on sperm function", Theriogenology 78(8): 1700-1708 (Apr. 20, 2012).

International Search Report and Written Opinion dated Aug. 23, 2019, for PCT/US2019/034601.

Kobayashi, H., et al., "DNA methylation errors at imprinted loci after assisted conception originate in the parental sperm", Eur. J. Human Genet. 17: 1582-1591 (May 27, 2009).

Mokin, M, et al., "Quantitative analysis of immunofluorescent punctate staining of synaptically localized proteins using confocal microscopy and stereology", Journal of Neuroscience Methods, vol. 157, Issue 2, pp. 218-224 (Oct. 30, 2006).

Moskovtsev, S.I., A. Qu, B.A. Cohen, R.A. Parkinson, J.Y. Zhang, A. Lee, C.L. Librach, "Preventing Fertility Failure in IUI with Kinetix Sperm Fc Receptor Test." Massachusetts Life Sciences Innovation Day (Boston, MA USA) Voted one of top 5 presentations (Jan. 6, 2017).

* cited by examiner

METHODS FOR DIAGNOSING FERTILITY OF EJACULATES FOR ARTIFICIAL INSEMINATION

CROSS REFERENCE TO RELATED APPLICATIONS

This application is a National Stage of PCT/US2019/034601, filed on May 30, 3019, titled: METHODS FOR DIAGNOSING FERTILITY OF EJACULATES FOR ARTIFICIAL INSEMINATION, which claims the benefit of U.S. Application No. 62/678,205, filed on May 30, 2018; both of which are incorporated herein by reference in their entirety.

BACKGROUND

1. Field of the Discovery

This application is directed to methods for diagnosing fertility of sperm samples for artificial insemination (AI), particularly intrauterine insemination (IUI).

2. Background Information

Treatment of mammalian semen to achieve a higher proportion of fertility in artificial insemination can be advantageous, particularly for couples who have tried to have offspring unsuccessfully by natural means. Infertility affects 10-15% of couples in the US, according to the Department of Health and Human Services, at an incalculable cost of human suffering. According to a 2015 report of the Practice Committee of the American Society for Reproductive Medicine (Fertility and Sterility vol 103), a male factor is contributory to 30-40% of infertility in couples, with some clinicians saying as high as 50% (Agarwal, 2015). Compounding these difficulties are the increasingly late times in life where people choose to bear children which creates advanced maternal age issues, as well as paternal age issues.

In human assisted reproductive clinics, couples have generally tried to obtain pregnancy for 6-12 months before being referred for an infertility workup. Infertility is generally defined by the World Health Organization as failure to achieve a clinical pregnancy after 12 months of regular unprotected intercourse. In such clinics, pregnancy typically is achieved, according to www.babycenter.com, only about 4-5% of the time using IUI and 7-16% using IUI plus fertility techniques. More expensive in vitro fertilization (IVF) procedures achieves positive results for each woman's cycle about 5-40% of the time, depending on age (21% success per cycle for women age 38-40). It would be desirable to increase the percent of positive pregnancies using the less expensive IUI procedure, which also prevents exposure to surgical risk and eliminates the need to culture human embryos in the laboratory prior to implantation.

The degree of variability in time course from semen samples collected from an individual makes the optimum for performing the sperm insemination procedure in IUI unpredictable. In addition, the way semen is processed in the human clinic significantly complicates real-time monitoring. The assay cannot be done with sperm when being centrifuged, a step never used with livestock. Thus, in some cases, preferably aliquots for assay taken before centrifugation are used, and therefore the sperm being assayed is not the same as that used for insemination (unlike for cattle). In addition, in human clinics the sample used for IUI is washed into synthetic medium to prevent cramping upon placement into the uterus, exposing the sperm to even more artificial conditions beyond centrifugation (which is known to negatively affect sperm) not found in the ejaculate.

Furthermore, sperm are subjected to both increases and decreases of temperature in the clinical laboratory, conditions that affect sperm biology which are not encountered in work with cattle semen, where temperature is controlled very differently. Furthermore, cattle doses are generally processed for frozen insemination, while human doses are processed for both frozen doses and also for fresh doses inseminated a variable number of hours after ejaculation. In contrast to work with cattle, for work in the human clinic a different sample is sometimes required for clinical analysis. Despite this different sample of sperm cells, they must nonetheless predict an appropriate sperm state in the cells intended for dosing (insemination) that are not assayed directly. The requirement does not exist in livestock insemination, where sperm from exactly the same container used for making doses is also used for laboratory testing.

It is understood that sperm analysis in human assisted reproductive clinics is currently practiced by evaluation of a single sample of untreated ejaculate at a single time point. This time point generally occurs before sperm have become capable of fertilizing an egg, as freshly-ejaculated mammalian sperm are infertile. Two important pieces of information vital to accurately judging sperm health and whether sperm have reached a suitable state for pregnancy-producing IUI dosing are therefore lacking: data on sperm behavior changes with time and data on sperm behavior changes that can be provoked. These changes occur, to greater or lesser extent, depending on sperm quality and sperm state.

There are many examples of how omission of this information is deleterious. For example, the shelf life of sperm doses that are not frozen, which is most of them in the pork industry and in certain seasons and/or regions of the world for dairy cattle, is never measured. This means some bad ejaculates may be used and negatively impact conception. In the human clinic, as aforesaid, where both fresh and frozen semen doses are utilized, medical decisions are based on a single set of data that are not representative of the ejaculate-to-ejaculate variation, the biological changes sperm in a single ejaculate undergo with time or undergo with provocation by specific agents in vitro. This single time point method of testing obscures any understanding of how sperm change with time or whether they are healthy enough to respond upon provocation with behavior changes typical of normal sperm. Noted experts in the field have decried the uselessness of current methods of sperm evaluation in the human clinic (Barratt, 2011) and also have expressed concern that more technically complex methods than IUI, specifically IVF and intra-cytoplasmic sperm injection (ICSI), may carry risks to babies born from IVF and ICSI (Kobayashi, 2009, Alukal, 2008).

The ability to assay sperm for the likelihood to produce fertility has historically been difficult or impossible. Current diagnostic tests include DNA fragmentation, motility, shape and number of sperm in ejaculate. However, these tests have proven unreliable for predicting fertility. A diagnostic method to determine the quality of sperm required for their fertilizing status to produce successful pregnancy would be highly beneficial. A diagnostic method to identify the capability of sperm to enter the state required to produce an IUI pregnancy is the critical missing infertility test. Without it, physicians must guess whether to subject a woman to a morbid surgical procedure to retrieve eggs, fertilize them in vitro, culture human embryos and reimplant them (IVF), or to simply perform on a woman a 5 minute procedure to introduce washed sperm into the uterus (IUI). The implications in terms of risk, cost and accessibility of the procedures is substantial. Many couples are subjected to unnecessary and highly risky drug regimens and surgical procedures when, in fact, IUI of sperm at the proper state would produce pregnancy.

Clearly, methods that provide tight correlation of sperm behavior with fertility are needed, as are means of increasing the fertility of sperm doses. A positive impact on medical cost reduction and medical risks to the woman can be added to the incalculable benefit derived by couples finally able to have a truly wanted child. The same is true in agriculture, where female livestock fertility is a key driver of on-farm profitability and also increases biosecurity by on-farm births instead of import of animals (and possibly diseases).

It would be desirable to have a better method for determining the quality of sperm in an ejaculate to produce fertility when inseminated into a female mammal.

SUMMARY

Sperm are very unusual cells in that they face a hostile environment that they must effectively overcome in order to achieve fertilization. Although not being bound by theory, it is believed that the hostile environment is deliberate, as it enables selection of the best sperm into the pool that will fertilize the egg. This would explain why sperm of higher quality, for example, those having better morphology, are found in the oviduct compared to the ejaculate (Ahlgren, 1975). Thus, the sperm go through various fertility states during maturation and life cycle.

It has been surprisingly and unexpectedly discovered that sperm in semen can exhibit a pattern of maturation in which cohorts or subpopulations of sperm show increasing (to a maxima) and decreasing (to a minima) biomarker expression. It has been discovered that the change in expression of the biomarker by the cohorts is associated with sperm maturation state and fertility quality (i.e., the ability to fertilize a female or an oocyte). It has also been discovered that successive groups of sperm act or mature cooperatively in cohorts, through cell behavior changes. As such, as described herein the cycling of cohorts of sperm in an ejaculate can be predictor of the fertility quality of semen, for example, for use in an infertility clinic, obstetrician-gynecologist (ob-gyn) or urologist office, home-based semen analysis or sperm bank. For example, is has been surprisingly discovered that sperm cohorts passing through a maxima of biomarker expression, e.g., a lectin or an Fc receptor, to a minima are of high fertility quality and demonstrate an enhanced ability to fertilize a female or an oocyte.

Accordingly, in an aspect, the present description provides methods capable of determining the fertility quality of sperm in an ejaculate to provide increased fertility in the form of pregnancy results. The methods described herein involve monitoring, in real time, changes in the metabolic status of sperm in a specific semen sample. In certain embodiments, the methods provide a means determining the fertility quality of semen for use in an infertility clinic, ob-gyn office or sperm bank.

In an embodiment, the disclosure provides a method for diagnosing ejaculate fertility quality to obtain improved pregnancy results by a time-based assay of a semen sample from a male, the time-based assay method comprising the steps of:
  i. providing a semen sample from a male, and incubating the sample under controlled conditions;
  ii. selecting a marker or biomarker that is indicative of fertilization quality of sperm, wherein expression of the marker or biomarker changes with time;
  iii. determining or detecting the level or amount of expression of the marker or biomarker in an aliquot of sperm from the semen sample at a plurality of time points, wherein the state of the sperm in the aliquot of the semen sample parallels that of the (bulk) semen sample; and
  iv. determining or detecting the number of times that the sperm in the aliquot of the semen sample express the marker or biomarker at a maxima (and/or a minima), thereby determining the fertility quality of the sperm.

In certain embodiments, the method includes a step of processing or administering the sperm that proceed through at least two cycles of expression of the marker or biomarker at a maxima (and/or a minima). In certain embodiments, wherein the sperm do not cycle through at least two marker or biomarker expression maxima (and/or minima), the method includes the step of administering an agent or modifying culture conditions to facilitate or enhance the maturation state or capacitation state of the sperm, and optionally administering the sperm to a female or to an oocyte.

In an additional aspect, the disclosure provides a method for diagnosing ejaculate fertility quality to obtain improved pregnancy results by a time-based assay of a semen sample from a male, the time-based assay method comprising the steps of:
  a. creating akinetic model, wherein creating said kinetic model includes:
    i. providing a semen sample from a male, and incubating the sample under controlled conditions;
    ii. selecting a marker or biomarker that is indicative of fertilization quality of sperm, wherein expression or amount of the biomarker changes with time;
    iii. determining or detecting the level or amount of expression of the marker or biomarker in an aliquot of sperm from the semen sample at a plurality of time points to provide a kinetic model of sperm maturational state based on the level or amount of expression of the at least one marker or biomarker, wherein the state of the sperm in the aliquot of the semen sample parallels that of the (bulk) semen sample;
    iv. determining or detecting the number of times that the sperm in the aliquot of the semen sample express the marker or biomarker at a maxima (and/or a minima), thereby determining the fertility quality of the sperm in the semen sample (or in a subsequent semen sample from the same male); and
  b. providing a semen sample to be tested, and detecting for expression of the at least one biomarker as performed in (a), and calibrating the at least one biomarker expression displayed by the semen sample to said kinetic model of biomarker expression from step (a) to correlate the at least one biomarker expression during sperm maturation or capacitation and gain of or enhanced fertility;
  c. calculating a time for freezing or preparing said semen sample or freezing or preparing a subsequent sample from the same male for use in insemination from the calibration, wherein at said time the sperm are optimized for fertilization quality for the procedure to be used, for example IUI; and
  d. processing or administering said semen sample or a subsequent sample (i.e., test sample) from the same male to an egg, a female, or combination thereof by an in vitro fertilization or artificial insemination method, e.g., IUI or IVF at about said time point of step (c), thereby optimizing said enhanced fertility of said semen sample or subsequent semen sample from the same male upon insemination of said semen sample.

In certain embodiments, the kinetic model includes a rate, time-course of capacitation or maturity state of sperm changes (as sperm transition and mature from the infertile state at ejaculation) based on the level or amount of expression of the at least one marker or biomarker In any of the aspects or embodiments, the methods include the step of treating said semen sample with at least one of a chemical or biological agent that modulates the rate of sperm change and/or capacitation, an environmental stimulus that modulates the rate of sperm change and/or capacitation, or an atmospheric condition that modulates the rate of sperm change and or capacitation.

The assay can be conducted on an aliquot of semen or an aliquot of washed sperm in a synthetic medium which, if desirable, allows one to assay sperm in wash medium and follow sperm that produce maturing cycles of sperm in the wash medium to determine the time for insemination. In any aspect or embodiment, the method can include a step of assessing the level of the biomarker by a detectable label which binds the biomarker or the ligand either directly or indirectly.

In another aspect of this embodiment, the semen sample is assayed for said marker at intervals ranging from 1, 2, 3, 4, 5, 10, 12, 15, 20, 25, 30 minutes or more, which can depend on the rate of change of expression of the marker, on the time required to perform the assay, etc. In a further aspect, the assay preferably utilizes an aliquot of the semen sample or an aliquot of sperm producing results correlated to the sperm in the dose from that semen sample or from a subsequent semen sample from the same male. In a further aspect, the assay preferably utilizes continuous monitoring.

In certain embodiments, step (iii) includes determining or detecting the level of expression of the biomarker for a predetermined amount of time, e.g., about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180 minutes or more. In certain additional embodiments, step (iv) of the method includes determining or detecting the number of times the sperm in the aliquot of the semen sample express the biomarker at a maximum or peak within the predetermined time of (iii).

In another aspect of the invention, the predetermined period of time for assaying the semen is set to allow time to detect at least two cycles of expression of the biomarker, wherein a cycle includes a maximum followed by a minimum and increasing expression to a following maximum. In certain embodiments, the predetermined time period for the method is about 2.5 hours.

In certain embodiments, the maximum is a biomarker expression level that is greater than about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150% or more as compared to baseline or a minimum. In certain embodiments, the minimum is a biomarker expression level that is the same or less than baseline or is below a peak or maximum expression level by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In another aspect of this embodiment, the biomarker is selected from, though not limited to fertility-associated antigen, soybean trypsin inhibitor, a ligand, a lectin, an enzyme, or a receptor, which is expressed on the surface of the sperm, or internally or both. In one embodiment, a ligand includes, but preferably is not limited to, a protein, a glycoprotein, a carbohydrate, a glycolipid, or a lipid, including ones detected by relative membrane fluidity rather than lipid molecular structure, as reflected for example in relaxation times of fluorescence polarization measurements, to distinguish different membrane regions, such as lipid rafts. In another embodiment the biomarker is selected from, though preferably not limited to, acrosome length, acrosome morphology, acrosome ruffling, expression of a cell surface molecule, electrostatic charge of said sperm, permeability of sperm membrane, a lipid, cholesterol, phosphatidylserine, a sugar, a protein, e.g., heparin, a fucosylated carbohydrate or protein modified with the same, a Lewis antigen, an intracellular ion, and bicarbonate.

In certain embodiments, the biomarker is a molecule present on the surface of the sperm or that is shed by the sperm into the medium surrounding the sperm, for example, a sperm Fc receptor (FcR) or Fc binding protein, CD46, a carbohydrate, glycoprotein, carbohydrate binding protein, proteoglycan, glycolipid, a lipid, or a lectin. As long as the marker used can be correlated to sperm fertilization ability, it can be used in accord with the present invention. In certain embodiments, the biomarker is a sperm Fc receptor on the surface of the sperm head. In certain embodiments, the biomarker is a sperm FcR, wherein the FcR is indicative of a fertility state of the sperm.

In another embodiment, there is a method for determining or diagnosing the fertility quality of a semen sample for insemination in a female by monitoring a change in the metabolic status of sperm in the semen sample during incubation, the method comprising the steps of:
i. selecting a marker that is indicative of a fertility status of sperm, wherein expression of the marker changes during said incubation,
ii. determining the level of expression of the marker by sperm of the semen sample at a plurality of time points during said incubation, wherein an aliquot of said sample is assayed at each time point, and
iii. determining the number of times during said predetermined period that said level of expression of said marker goes through a level of expression corresponding to a maximum level of Fc expression of the sperm followed by said marker going through a level of expression corresponding to a minimum level of FcR expression of the sperm, thereby determining the fertility quality of the semen sample for insemination to provide improved pregnancy results In an embodiment, a method for diagnosing the fertility quality of newly collected semen ejaculate for obtaining improved positive pregnancy results comprises the steps of:
i. collecting a semen ejaculate,
ii. removing a small portion of the collected semen for assaying aliquots of sperm of said ejaculate over time for expression of a Fc receptor marker indicative of a fertility stage of said sperm,
iii. determining the number of times the marker passes through a maximum of expression,
iv. thereby determining the fertility quality of said semen for insemination of a female or egg to obtain improved positive pregnancy results, and optionally processing or administering the sperm having an enhanced fertility quality.

In any aspect or embodiment, the sperm sample is incubated at a constant temperature to temperature range of ambient to 37 C during the determining or detecting (monitoring) of the biomarker for the metabolic status.

In one embodiment, binding of a first ligand evokes the appearance of a secondary biomarker, which is detected by contacting a secondary marker with a supplemental ligand. Alternatively, assays in accord with the present invention can be conducted with agents that do not bind, but enter the sperm or interact in some other way (such as lipid insertion into one of the lipid bilayers on the sperm) to provoke a change with time that can be monitored, preferably for a detectable change.

In another non-limiting aspect of this embodiment, the permeability of a dye by said sperm or fragments thereof is assayed in an aliquot of said sperm sample by monitoring by the intensity of said dye in the sperm or fragments thereof. Sperm are known to bind seminal plasma agents onto the sperm membrane. It has now been found that sperm actually can imbibe agents from their surrounding medium. Therefore, fragments of sperm should be construed to include agents sperm acquire as cargo, not just sperm as formed in the testis or epididymis.

In another aspect of embodiments of the invention, the expression of a cell surface biomarker is monitored, and the time point selected to process the semen sample is determined with respect to an earlier time point when the sample maximally expresses the biomarker.

In another aspect of embodiments of the invention, the expression of a cell surface biomarker is monitored, and the time point selected to process the semen sample is determined with respect to the earlier time point when expression of said biomarker in said sample has decreased relative to a peak expression and subsequently begins to increase from a minimum in the expression.

In one embodiment, the described method is based on the percentage of sperm in the semen sample having a specified biomarker. In one aspect, the specified biomarker is a biochemical marker, which is optionally present on the cell surface. Regardless, the biomarker reflects or is indicative of the metabolic fertility status of the sperm. In certain embodiments, the marker is not limited to a sperm specific marker.

In another aspect, the description provides a method for determining the percentage of sperm in the semen sample having the biomarker that reflects the metabolic fertility status of the sperm. The assay comprises the steps of a) removing an aliquot from the semen sample; b) contacting the aliquot with a first ligand to said biomarker; c) detecting binding of said ligand by said sperm or fragments thereof; and d) determining the percentage of sperm in said aliquot which binds the ligand. In an alternative aspect of this embodiment, step d) can be replaced by the step of assessing the level of the biomarker by a detectable label which binds the biomarker or the ligand either directly or indirectly.

In another aspect the description provides a method of determining the concentration of said biomarker detected in sperm of said semen sample comprising: a) removing an aliquot from the semen sample; b) contacting the aliquot with a first ligand to said biomarker; c) detecting binding of said ligand by said sperm or fragments thereof; and d) determining the amount of biomarker expressed by sperm in said aliquot by quantitating the binding of the biomarker by the ligand; thereby determining the concentration of said biomarker detected in sperm of said semen sample.

In any of the aspects or embodiments described herein, the ligand is labeled directly or indirectly with a detectable label, preferably a visible label. In any of the aspects or embodiments described herein, detecting the binding of the ligand by the sperm includes detecting label bound directly or indirectly to the sperm, or fragments of the sperm. In any of the aspects or embodiments described herein, a sperm fragment is either associated or disassociated from intact sperm and may undergo further subsequent fragmentation. In any of the aspects or embodiments described herein, detecting the binding of the ligand by the sperm encompasses contacting the sperm in the aliquot with a second ligand which binds to the first ligand. In any of the aspects or embodiments described herein, the first ligand and/or the second ligand is an antibody. In any of the aspects or embodiments described herein, the antibody can be either polyclonal or monoclonal antibodies, and can comprise one or more labels.

BRIEF DESCRIPTION OF THE DRAWINGS

FIG. 3A: fresh ejaculate where all sperm are in reserve and very few are FcR positive. FIG. 3B: a group of sperm (cohort) in unison become positive for FcR detectable on the surface of the acrosome. FIG. 3C: the positive sperm begin shedding FcR and the sperm become less positive for the FcR on their surfaces. FIG. 3D: the spent sperm that have shed almost all their FcR now appear negative. FIG. 3E: a new group of sperm (cohort) initiates maturation from the reserve pool, in the presence of pre-existing shed FcR that wards off female immune attack of the "foreign" sperm. FIG. 3F: the second cohort of sperm in unison become positive for FcR on the surface of the acrosome.

DETAILED DESCRIPTION

Figure 1A:
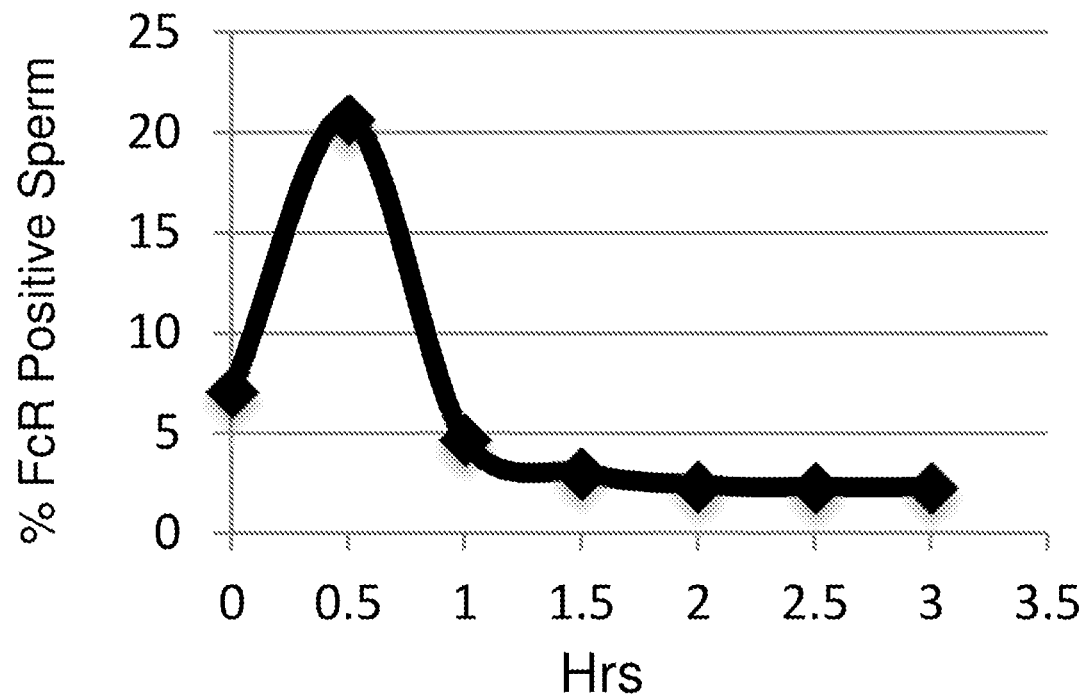
FIGS. 1A-1C are graphs illustrating % sperm that are FcR positive versus time for samples of abnormal sperm.

In accordance with this detailed description, the following abbreviations and definitions apply. It must be noted that as used herein, the singular forms "a", "an", and "the" include plural referents unless the context clearly dictates otherwise. Thus, for example, reference to "an antibody" includes a plurality of such antibodies, and so forth. Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods (see generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4, Ed, John Wiley & Sons, Inc. See Harlow and Lane, Antibodies: A Laboratory Manual, Cold Springs Harbor Publications, New York, (1988) which are incorporated herein by reference) and chemical methods. Unless otherwise stated, all ranges described herein are inclusive of the specific endpoints. The following terms are provided below.

As used herein, the term "fertility quality" with respect to sperm includes, but is preferably not limited to, a physiological "swim up" or motility characteristic of the sperm or a subgroup of the sperm as reserve sperm, spent sperm and a group of sperm moving in synchrony through a cycle measured by the assays described herein are often simultaneously present. The desired trait can be expressed before fertilization, e.g., the trait of being in a physiologic state capable of fertilization, such state varying with the type of fertilization employed.

As used herein, the term "semen sample" includes any semen sample collected from an ejaculate of any mammal, including, but preferably not limited to, human, cattle, goats, sheep, buffalo, swine, horses, cats, dogs, rat, mouse, rabbits, hamsters and endangered species of mammals. Preferably the sample is incubated at a relatively constant temperature immediately after collection and the time-based assay of the present invention is conducted.

As used herein, the term "metabolic status" or "metabolic state" or "metabolic stage" or "sperm state" is a physiological state of the sperm with respect to specific biochemical and biophysical properties at a specific time point during the incubation period of the sperm sample. Typically, the physiology of sperm changes over time with age after collection. Thus, changes in physiology or metabolic state of sperm in a semen sample can include expression of a biomarker that correlates to the fertility state. Additionally, changes in physiology or metabolic state of sperm in a semen sample can be reflected by expression of one or more biomarkers. In one embodiment of the methods disclosed herein, the expression of one or more biomarkers occurs earlier than the expression of the desired trait; i.e., the enhanced ability to fertilize a female or an oocyte.

Thus, the phrase "a biomarker indicative of a metabolic fertility state of sperm" refers to a measurable attribute of a sperm and/or group of sperm, including but not limited to a physiological, structural, functional, biochemical and/or electrochemical attribute which reflects the metabolic status of the sperm at a particular time point.

As used herein, the term "maker" or "biomarker" includes any attribute that correlates with the fertility status of sperm. In certain embodiments, the biomarker can be a feature that correlates with FcR expression of sperm. The term "marker" or "biomarker" includes, but is preferably not limited to, a structural, physical, electrophysical, or biochemical attribute of sperm and/or fragments thereof, including, for example, the nonlimiting examples of acrosome length, sperm morphology (ruffling) of the sperm, expression of a cell surface molecule on the sperm, electrostatic charge of sperm, and permeability by sperm to a molecule, such as, for example, but not limited to, a dye. The term "biomarker" further includes, but is not limited to, a ligand, a lectin, an enzyme and a receptor, which is expressed on the surface of the sperm, or internally, or both. In some embodiments, the biomarker is a morphological change in an acrosome which can be viewed, for instance, using bright field microscopy. With respect to acrosome morphology, over time the surface of the acrosome's membrane appears increasingly ruffled. In some embodiments a biomarker can be cryptic at some stages of metabolism, and not detected.

As used herein, the term "antibody," includes, but is not limited to a polypeptide substantially encoded by an immunoglobulin gene or immunoglobulin genes, an IgG antibody, an IgM antibody, or a portion thereof, which specifically bind and recognize an analyte, antigen or antibody or binds non-specifically via the Fc fragment. "Antibody" also includes, but is not limited to, a polypeptide substantially encoded by an immunoglobulin gene or immunoglobulin genes, which specifically binds and recognizes the antigen-specific binding region (idiotype) of antibodies produced by a host in response to exposure to the analyte. In one embodiment of the methods described herein, an antibody binds the sperm or fragments thereof, or a primary antibody, through a site on the antibody other than its paratope. In another embodiment, the antibody binds the sperm or fragments thereof, or a primary antibody through its paratope. In another embodiment of the methods described herein, an antibody binds the sperm or fragments thereof, or a primary antibody, both through its paratope and through a site on the antibody other than its paratope.

As used herein, the term "antibody," encompasses polyclonal and monoclonal antibody preparations, as well as preparations including monoclonal antibodies, polyclonal antibodies, hybrid antibodies, altered antibodies, F(ab')$_2$ fragments, F(ab) fragments, F$_v$ fragments, Fc fragments, single domain antibodies, chimeric antibodies, humanized antibodies, dual specific antibodies, bifunctional antibodies, single chain antibodies, and the like, and functional fragments and multimers thereof, which retain specificity for an analyte or antigen. For example, an antibody can include variable regions, or fragments of variable regions, and multimers thereof, which retain specificity for an analyte or antigen. See, e.g., Paul, Fundamental Immunology, 3rd Ed., 1993, Raven Press, New York, for antibody structure and terminology. The antibody or portion thereof, may be derived from a bird or any mammalian species, e.g., from a mouse, goat, sheep, rat, human, rabbit, or cow antibody. An antibody or fragments thereof, may be produced synthetically by methods known in the art, including modification of whole antibodies or synthesis using recombinant DNA methodologies, including using phage display libraries. In preferred embodiments, the "antibody" binds to an Fc receptor on the surface of the sperm head.

The following is standard for traditional Ag/Ab interactions.

In a preferred embodiment of the present invention, the antibody binding is by the Ab region, e.g. through Fc region (especially fucose-containing). Thus, high affinity is not required for the practice of the present invention.

As used herein, the phrase "binds to" refers to an antibody, reagent or binding moiety's binding of a ligand with a binding affinity ($K_a$) of $10^6$ M$^{-1}$ or greater. As aforesaid, high affinity binding is not required for the practice of the present invention. It is important for the ligand to complex with the receptor. The binding affinity of an antibody can be readily determined by one of ordinary skill in the art (for example, by Scatchard analysis). A variety of immunoassay formats can be used to select antibodies specifically immunoreactive with a particular antigen. For example, solid-phase ELISA immunoassays are routinely used to select monoclonal antibodies specifically immunoreactive with an analyte. See Harlow and Lane, Antibodies: A Laboratory Manual, Cold Springs Harbor Publications, New York, (1988) for a description of immunoassay formats and conditions that can be used to determine specific immunoreactivity. Typically a binding reaction will be at least twice background signal to noise and more typically more than 10 to 100 times greater than background. In the case of the practice of the present invention, binding affinity may be increased by complexation of first and second ligands.

As used herein, the term "label" includes a detectable indicator, including but not limited to labels which are soluble or particulate, metallic, organic, or inorganic, and may include radiolabels (such as, e.g., $^{14}C$, $^3H$, $^{32}P$), enzymatic labels (e.g., horseradish peroxidase, galactosidase, and other enzyme conjugates), spectral labels such as green fluorescent protein, fluorescent dyes (e.g., fluorescein and its derivatives, e.g., fluorescein isothiocyanate (FITC), Alexa Fluor® 488 Dye, which is a green-fluorescent dyes conjugate with nearly identical spectral properties and quantum yield as fluorescein isothiocyanate, rhodamine, Yo-Pro, a carbocyanine nucleic acid stain sold by Invitrogen, catalog Product V13243, the green-fluorescent YO-PRO®-1), chemiluminescent compounds (e.g., luciferin and luminol), spectral colorimetric labels such as colloidal gold, or carbon particles, or colored glass or plastic (e.g. polystyrene, polypropylene, latex, etc.) beads, as well as dyes, including the cell-permeant pH indicator, carboxy SNARF®-1, an acetoxymethyl ester, acetate which has a pKa of ~7.5 after de-esterification and is sold by Invitrogen, as catalog #PPLM63-C1270. Where necessary or desirable, particle labels can be colored, e.g., by applying dye to particles. In preferred embodiments the "label" is a visible label.

As used herein, the term "colored particle label" includes, but is not limited to colored latex (polystyrene) particles, metallic (e.g. gold) sols, non-metallic elemental (e.g. Selenium, carbon) sols and dye sols. In one embodiment, a colored particle label is a colored particle that further comprises a member of a conjugate pair. Examples of colored particles that may be used include, but are not limited to, organic polymer latex particles, such as polystyrene latex beads, colloidal gold particles, colloidal sulphur particles, colloidal selenium particles, colloidal barium sulfate particles, colloidal iron sulfate particles, metal iodate particles, silver halide particles, silica particles, colloidal metal (hydrous) oxide particles, colloidal metal sulfide particles, carbon black particles, colloidal lead selenide particles, colloidal cadmium selenide particles, colloidal metal phosphate particles, colloidal metal ferrite particles, any of the above-mentioned colloidal particles coated with organic or inorganic layers, protein or peptide molecules, or liposomes. For example, Quantum dots sold by Sigma-Aldrich, is a label encompassed herein.

As used herein unless the context suggests otherwise, the term "decreased expression" with respect to a marker, can mean a decrease in expression (including a decrease in accessibility or an increase in crypticity) of a marker or biomarker or given measurable activity (e.g., binding activity, membrane permeability, electrostatic charge) by at least 5% relative to a reference. In certain embodiments a decreased expression or activity is down regulated by at least 5%, 10%, 15%, 20%, 30%, 40%, 50%, 60%, 70%, 80%, 90%, or more, up to and including 100%, i.e., complete absence of the given expression or activity. Decreased expression of a marker can be measured as described in the working examples herein. The term "increased expression" refers to an increase in expression of a marker or given measurable activity (e.g., binding activity, membrane permeability, electrostatic charge) by at least 5% relative to a reference, for example, at least 10%, 15%, 20%, 30%, 40%, 50%, 60%, 70%, 80%, 90%, 100% or more. An increased expression or activity of a marker can be measured as described in the working examples herein.

As used herein, the term "fertility" with respect to sperm in a semen sample, refers to the ability of the sperm to fertilize an egg and create a viable embryo, it may not live to fetus stage. This ability changes with conditions and as the sperm age and with method of insemination or fertilization, as non-limiting examples IUI and IVF or IVF/ICSI (IVF with intracytoplasmic sperm injection).

As used herein, the term "punctate staining" means a distribution of detectable label in the form of distinct spots or points as opposed to a uniform staining across the surface of a sperm or fragments thereof. Quantitative analysis of punctate staining is known in the art, as described for example by Maxim Mokin and Joyce Keifer in "Quantitative analysis of immunofluorescent punctate staining of synaptically localized proteins using confocal microscopy and stereology", Journal of Neuroscience Methods, Volume 157, Issue 2, 30 Oct. 2006, Pages 218-224. Changes from punctate staining to stained ridges on the sperm (like mountain ranges) can be seen as puncta that coalesce with time in most cases.

As used herein, the term "pregnancy" refers primarily to clinical pregnancy results, meaning detection of a fetal heartbeat at 6 weeks. In a single case, the term refers to biological pregnancy, meaning an increase in the amount of human chorionic gonadotrophin present in blood as a pregnancy marker. In both forms of pregnancy, a sperm has successfully fertilized an egg.

Increased positive pregnancy results is a desired goal for assisted reproductive clinics, Ob/Gyn offices, and sperm banks and economically desired by couples seeking reproductive aid. It is understood that positive pregnancy results in IUI procedures typically are about 4-16% of the procedures per ovulatory cycle, meaning couples wanting offspring typically conceive within 7 IUI cycles according to The Sperm Bank of California, each at a financial as well as emotional cost. Then, if IUI is unsuccessful, the couple must consider IVF procedures at considerably more cost, which in many cases (and currently 35 states), is not covered by insurance.

As indicated above, it has been surprisingly and unexpectedly discovered that the pattern of cycling of cohorts of sperm in an ejaculate can be predictor of the fertility quality (i.e., ability to fertilize a female or oocyte) of semen, for example, for use in an infertility clinic, obstetric-gynecologist (ob-gyn) office or sperm bank. It has also been discovered that successive groups of sperm act in unison cooperatively in cohorts, through cell behavior changes.

Depending on how sperm are processed, the cycle state at administration may vary. For example, one wants to administer when sperm are at or near an FcR minimum, by predicting around a detectable maximum, when that minimum will occur. But even seeing ejaculate behavior and then treating the male differently, without administering that ejaculate, has diagnostic value. For example, if the male's sperm non-cycling, the method of treatment includes administration via IVF. Banks can sell rapid cyclers at a premium for use in IUL. They can divert non-cyclers to IVF use when the frozen doses are sold to clinics.

Differences between a natural insemination process and a human assisted IUI clinical process include at least the following differences. In the natural process, the male ejaculates the semen directly into the vagina. In the IUI process, washed sperm in a synthetic medium is injected into the uterus. In the natural process, semen and mucus act as protective agents as the sperm matures during deposit into the vagina and swim up through the cervix into the uterus, and possibly during storage of a pool of reserve sperm in the cervix, such pool being prevented from forming by IUI. In the IUI process, the maturation status of sperm is not known and the coordination of sperm maturation with female tract location is interfered with by washing procedures so that the sperm is introduced into the uterus at various fertility states including states incompatible with pregnancy. In the natural process semen is inseminated into the vagina and temperature of the sperm is controlled relatively at body temperature (about 37° C.), whereas in the IUI process there can be multiple decreases and increases in the temperature at which sperm is kept prior to injection into the uterus. In the normal process, the sperm are exposed to reduced oxygen tension due to lower amounts of oxygen in the female tract and presence of semen (Fischer, 1993), whereas the IUI process exposes sperm to ambient oxygen for relatively long periods prior to injection into the uterus, potentially raising the known risk to sperm of oxidative damage (Guthrie, 2012). In some cases of IUI, only part of the ejaculate—and therefore a reduced sperm number relative to natural insemination—is used due to volume restrictions, and sample removed for laboratory analysis, whereas in natural insemination the entire ejaculate is deposited. In the natural process Fc receptors on the sperm mature and are present in the semen, whereas in the IUI process Fc receptors in the semen are washed away with semen during processing for insemination into the uterus.

Currently used tests for fertility quality of sperm include a one-time assessment of DNA fragmentation (optionally), motility, shape and number of sperm in the semen. These current standard tests can determine that some semen samples are unsuitable for fertility in some AI procedures, but are not useful in predicting fertility quality. Passing these standard tests does not mean that the semen is capable of producing fertility when inseminated into a female. The capability of producing fertility is conferred by sperm state of the ejaculate, which varies as measured by practice of the present invention such that the same ejaculate may by turns be—cyclically—both incapable and capable of producing fertility at different times. Applicants have discovered a better diagnostic for determining the fertility quality of sperm is provided by counting the cycles of expression of a marker using the time-based assay described herein.

Applicants have discovered a better diagnostic for determining the fertility quality of sperm. By counting the cycles of expression of a marker using the time-based assay described herein, the amount of sperm that are capable of producing fertility when inseminated into a female is enhanced. In accord with the present disclosure as aliquots of the collected ejaculate are assayed at preselected time intervals after collection of the semen, fertility quality of the sperm can be determined by observing that the expression of the Fc receptor marker by sperm fluctuates through a maximum followed by a minimum, and then increases in expression. The biological expression of the Fc receptor marker over time correlates with fertility quality of the sperm.

Without being bound by any particular theory, the inventors hypothesize that a semen sample has multiple cohorts (sub-populations) and that the cohorts of sperm in the semen activate during different periods of time to create the sperm fertility cycle and that activation and aging of one cohort typically is followed by activation and aging of a second cohort of sperm in the semen, and may be followed by a third cohort, and possibly more cohorts. In the present disclosure, the time based assay detects cohorts of sperm sequentially by cycles of a marker that correlates to FcR deployment to provide a meaningful improvement diagnosing fertility quality of sperm for use in assisted reproduction to improve outcome.

Figure 1B:
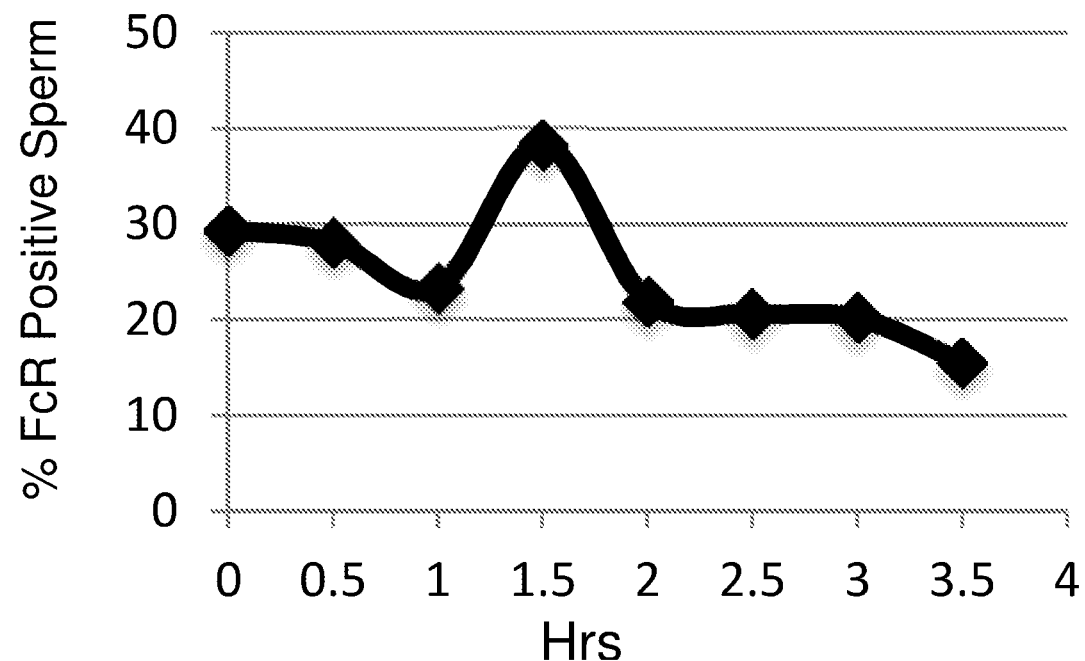
Figure 1C:
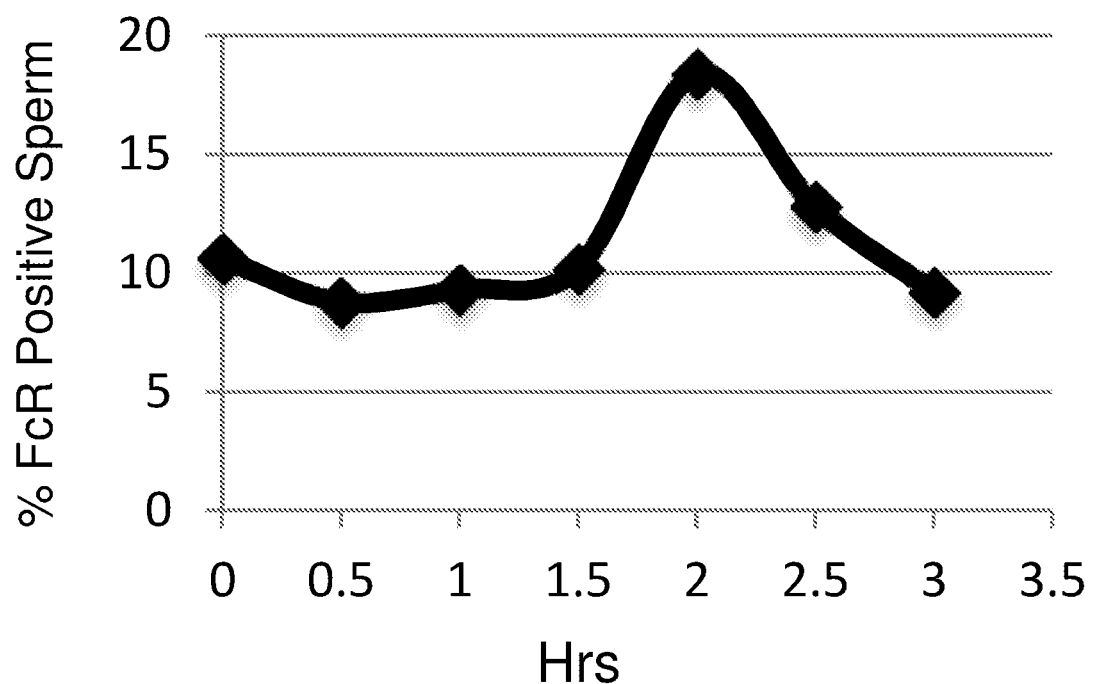

FIGS. 1A-1C illustrate graphs for time-based assays showing sperm of donors where the sperm exhibit characteristics that make the sperm highly unlikely to produce pregnancy. The semen exhibits the inability to demonstrate multiple cohorts of sperm cycling over a time period as determined by the detection of a marker that correlates with fertility quality, i.e., fertilization ability, e.g., the amount of sperm FcR Thus, use of the time-based assay can diagnose sperm capability of quality for producing pregnancy, particularly for use in treatments that demand more of sperm performance such as timed intercourse with use of female fertility drugs and IUI, in contrast to risky techniques that require surgery, that work with more compromised sperm, such as IVF and IVF/ICSI.

Assays in accord with the present disclosure allow compensation for the changes introduced by IUI that differ from natural insemination. Without sperm fertility state adjustment, these changes might otherwise lead to introduction of sperm, into the highly selective uterine environment, at a state that is incompatible with production of pregnancy.

Sperm undergo a maturation process upon ejaculation. Based on the inventor's observations, sperm mature in groups (cohorts) as determined by FcR biochemistry. This is consistent with fully mature activated sperm having a short life during which they can fertilize an egg, or they will die (Cohen-Dayag 1995). Assays in accord with this invention detect, or correlate with, the presence of the sperm FcR expression which appears on the sperm head during sperm maturation and then is shed from sperm. At intervals of 1-2$h$, typically a second cohort matures. Thus, the FcR marker can be used to determine the maturation and thus fertility of a group of sperm to be used therapeutically. The marker can also determine the capacity of sperm in an ejaculate to undergo maturation, in a nonlimiting example, with respect to normal number of cohorts, normal cohort shape of curve, normal kinetics of FcR initial expression, average percentage of FcR expression as a function of sperm count, and percent of population expressing, in a diagnostic setting. With this knowledge, it is possible diagnose the fertility quality of semen. Thus, patients may be stratified into pre-ART (IUI) or ART (Assisted Reproductive Technology) procedures based on sperm fertility quality.

Even though maturation of sperm cohorts can vary significantly from individual to individual and even for different ejaculates from the same individual, it has been surprisingly and unexpectedly discovered that the time interval between an earlier metabolic state reflected by maximum expression of the Fc receptor marker and the later expression of the desired "fertility state trait" (i.e., fertilization quality or ability to fertilize a female or an oocyte) is relatively consistent for semen samples collected within a relatively close time frame (1 day to less than 30 days) from individuals and incubated under the same conditions. This consistent time interval between fertility states of a single maturing cohort of sperm is used in the real time methods described herein to determine when sperm of each individual semen sample will express the desired fertility state trait by monitoring expression of one or more markers.

In certain embodiments, the disclosure provides methods comprising collecting a semen sample. Inspecting, visually inspect for viability. The sample can be neat semen or washed sperm resuspended in supportive medium. In a preferred embodiment, reagents are stored at 22-26° C. and semen or washed sperm are stored at 37° C. with some exposure to ambient laboratory temperature, and allowing the semen to liquefy, which requires about 30 minutes from production (consistent with current procedures), but it is preferred to begin testing immediately. Remove a 50 μL sample for aliquots for the assay testing or test from the larger aliquot reserved for standard laboratory analysis. Preferably prepare the assay in this order:
  a. place 100 μL of GREEN 1, 20 μL of RED 2, 10 μL neat semen (or washed semen), 5 μL BLUE 3 into 1.5 mL tube.
  b. in certain embodiments this procedure is repeated at regular intervals of every 15 or 30 minutes and reagents at or near ambient, preferably not ice cold for assays because there is concern that cold reagents (for example on ice) can cause an artifact through temperature shock. However, cold reagents may be used after the first time point or two, if and only if the ejaculate is cooled after collection. This is common in some applications but not others.

Thus, for example, in step (a), one hundred (100) μl antibody diluent with Bovine Serum Albumin (Invitrogen SKU #00-3118) (GREEN 1) is mixed with twenty (20) μl of primary antibody (rabbit anti-*Salmonellas* spp; *Salmonella* H antiserum A-Z product number 224061; Difco, Detroit, MI; reconstituted according to the manufacturer's instructions or to the manufacturer's required volume with wash buffer, PBS Tablets without calcium without magnesium (MP Biomedicals catalogue no. 2810305) (RED 2), followed by 5 μl of secondary antibody conjugated to Alexa Fluor® 488 (goat anti-rabbit IgG (H+L); Invitrogen, Carlsbad, CA, catalogue no. A11008, (now Thermo Fisher Scientific)) (2 mg/1) (BLUE 3). Examples of other diluents (GREEN 1) useful in the practice of this invention include: phosphate buffered saline (the current Arex wash buffer), HTF HEPES culture medium with EDTA and glutamine (InVitroCare catalog #2002), Quinns(™) Sperm Washing Medium (Origio catalog #ART-1006) and other supportive buffered cell-supportive media. Other antibodies (RED 2) include: any having an Fc receptor that can be used in the assay, including: Difco antiserum for microbiological testing, for example, BD Difco *Salmonella* O Antiserum Poly A-I & Vi (BD Difco catalog #222641, and ChromPure Rabbit IgG, Fc Fragment (Jackson ImmunoResearch catalog #011-000-008), as well as IgM molecules. Other conjugants (BLUE 3) include: Goat Anti-Rabbit IgG (H+L), DyLight (™) (Thermo Fisher Scientific catalog #35552), and secondary antibodies conjugated with FITC or other fluorophores for which cytometer excitation and emission filters are chosen to be suitable.

Figure 2A:
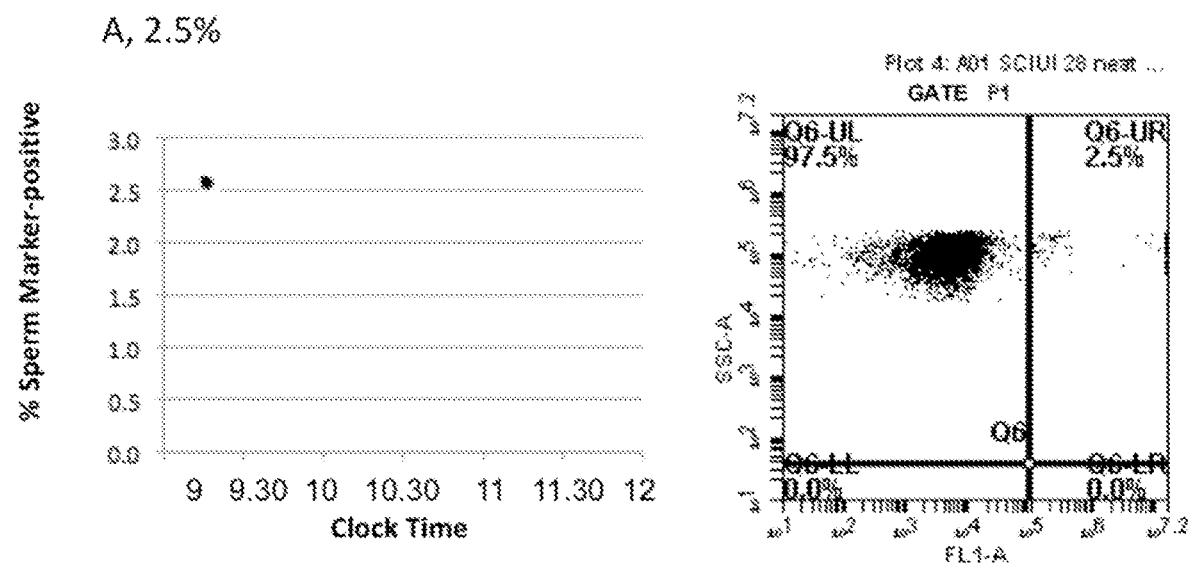
FIGS. 2A(1)-2F(2) illustrate cytometer images and readings with corresponding plots of % sperm FcR positive versus time for an exemplary time-based assay.
Figure 2B:
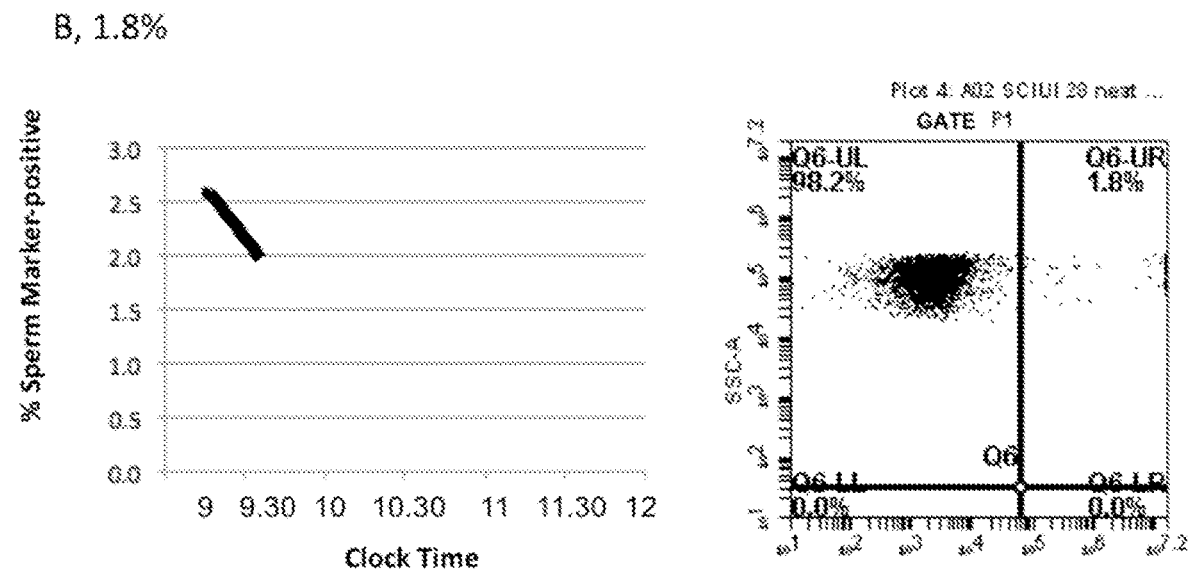
Figure 2C:
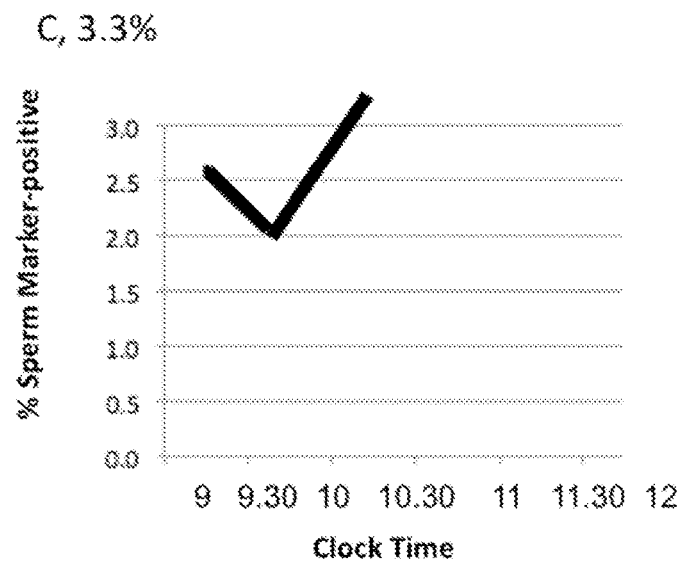
Figure 2C:
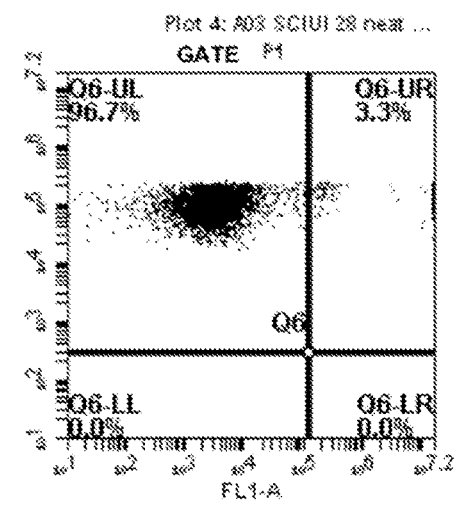
Figure 2D:
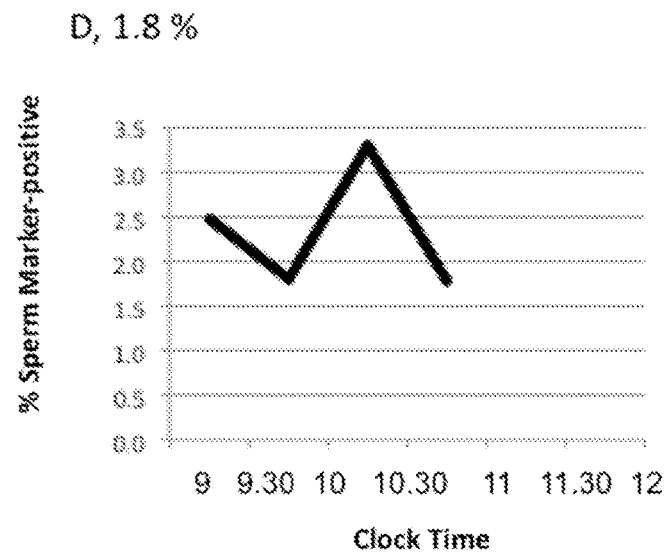
Figure 2D:
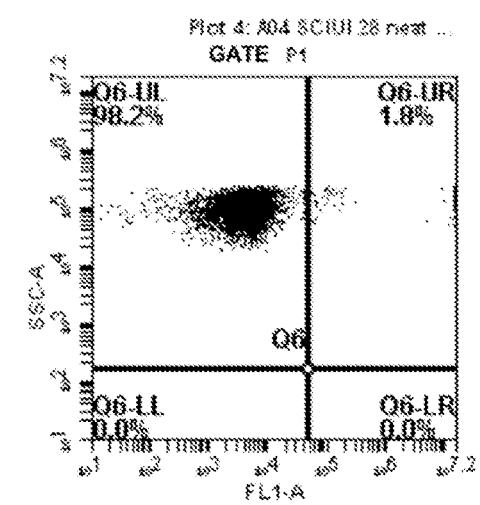
Figure 2E:
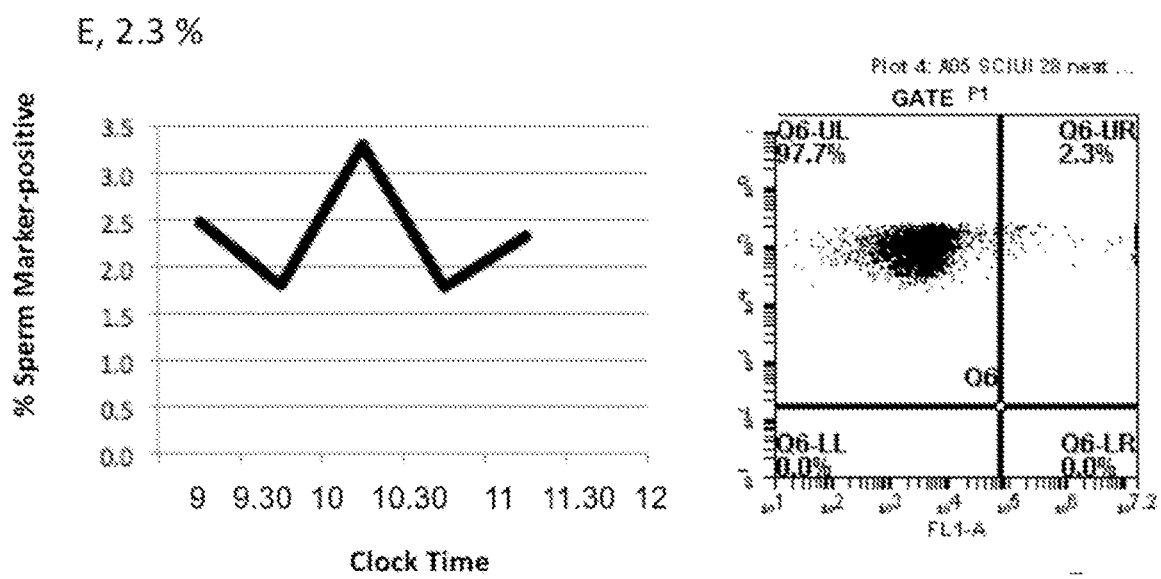
Figure 2F:
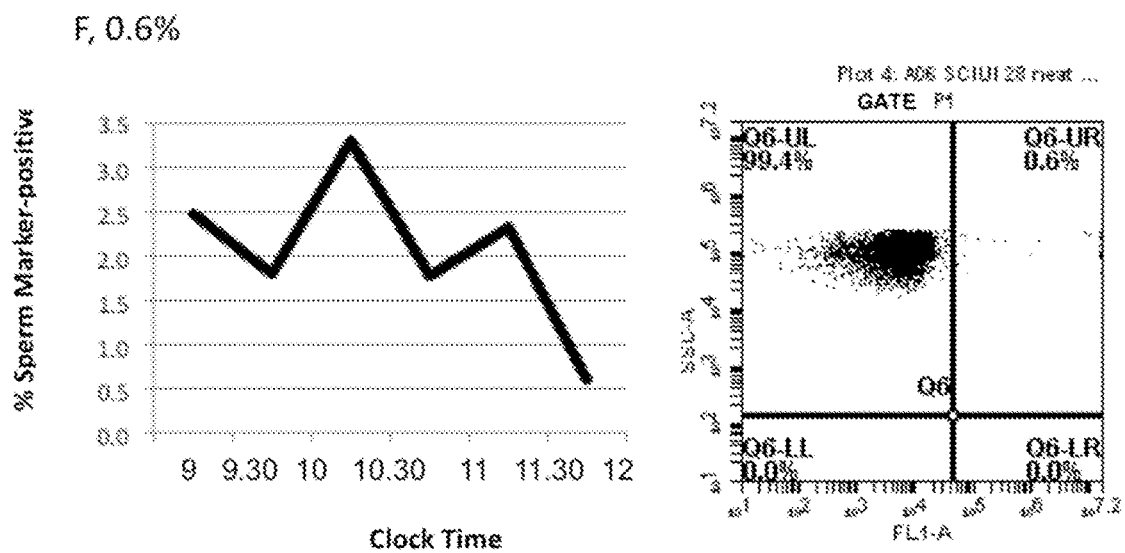
Figure 3A:
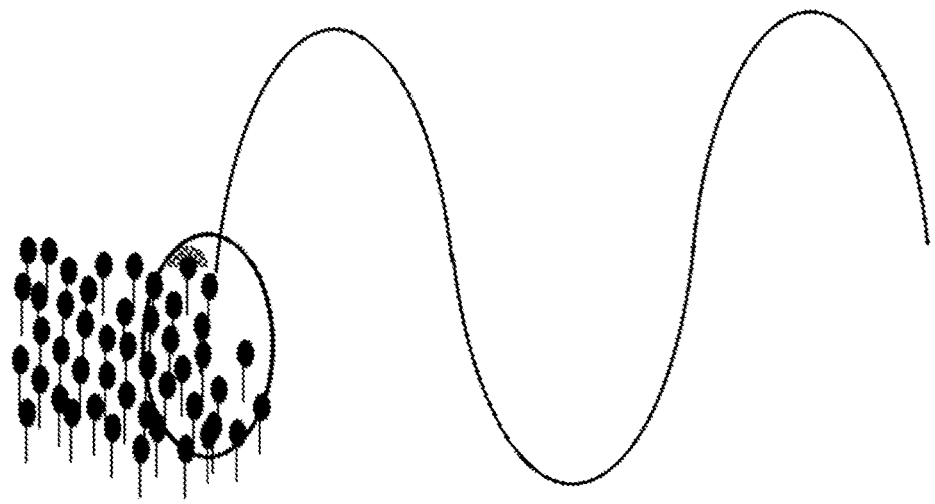
FIG. 3A-3F illustrate the maturation of groups of sperm in synchrony through the FcR cycle, which takes about 1 hour to complete for each group of sperm as they move through each cycle in succession.
Figure 3B:
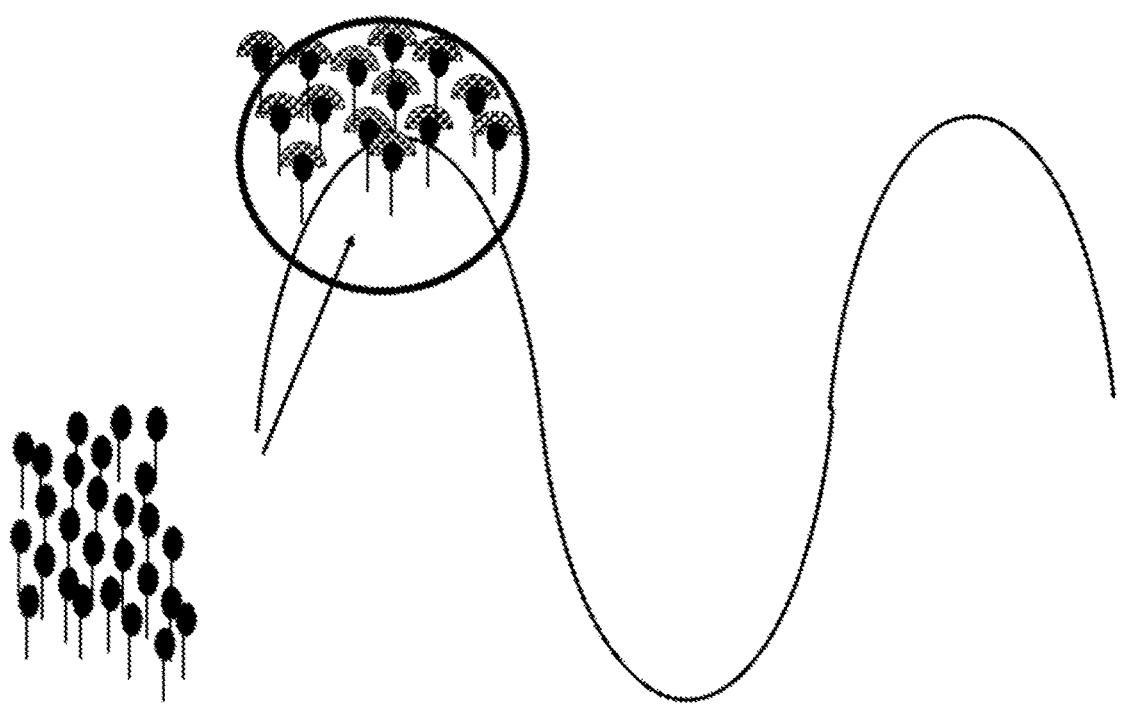
Figure 3C:
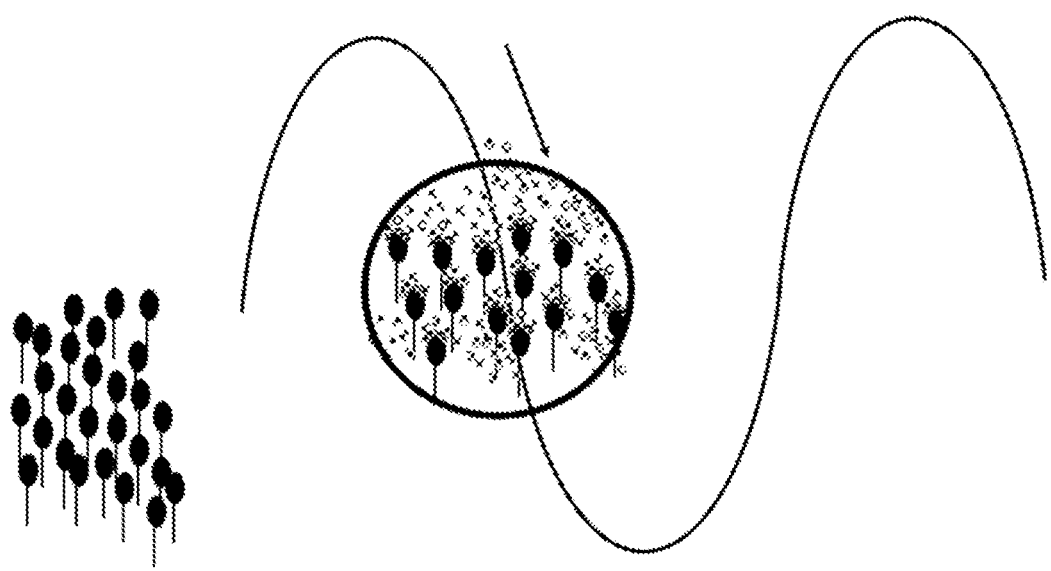
Figure 3D:
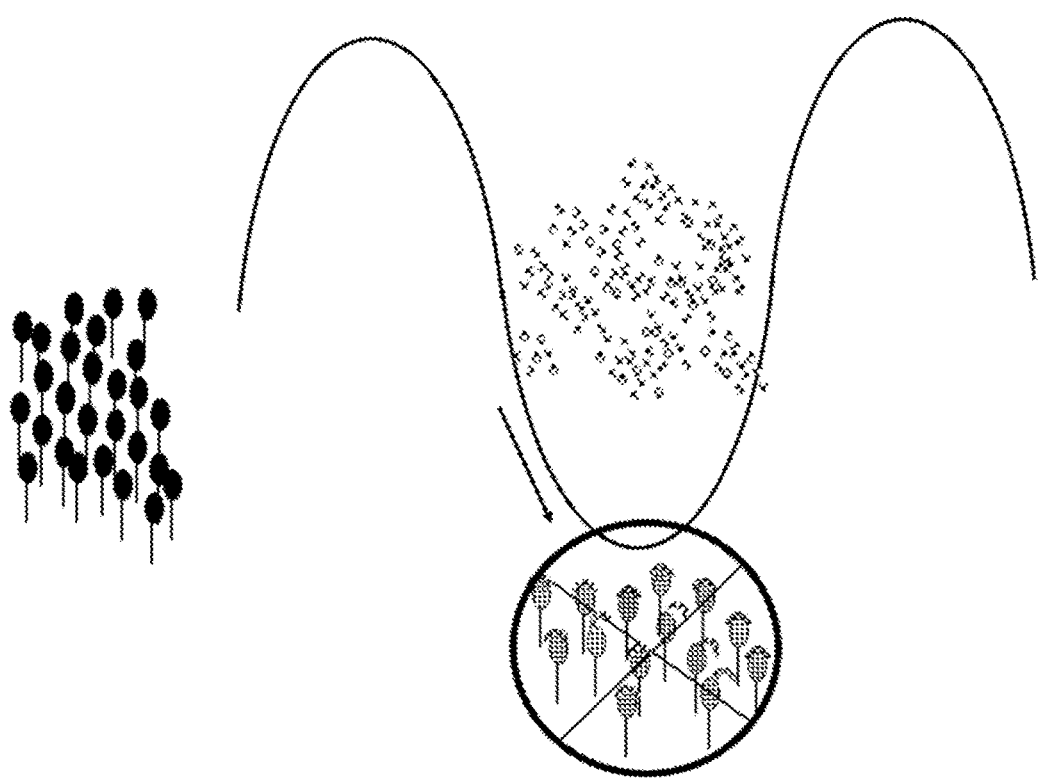
Figure 3E:
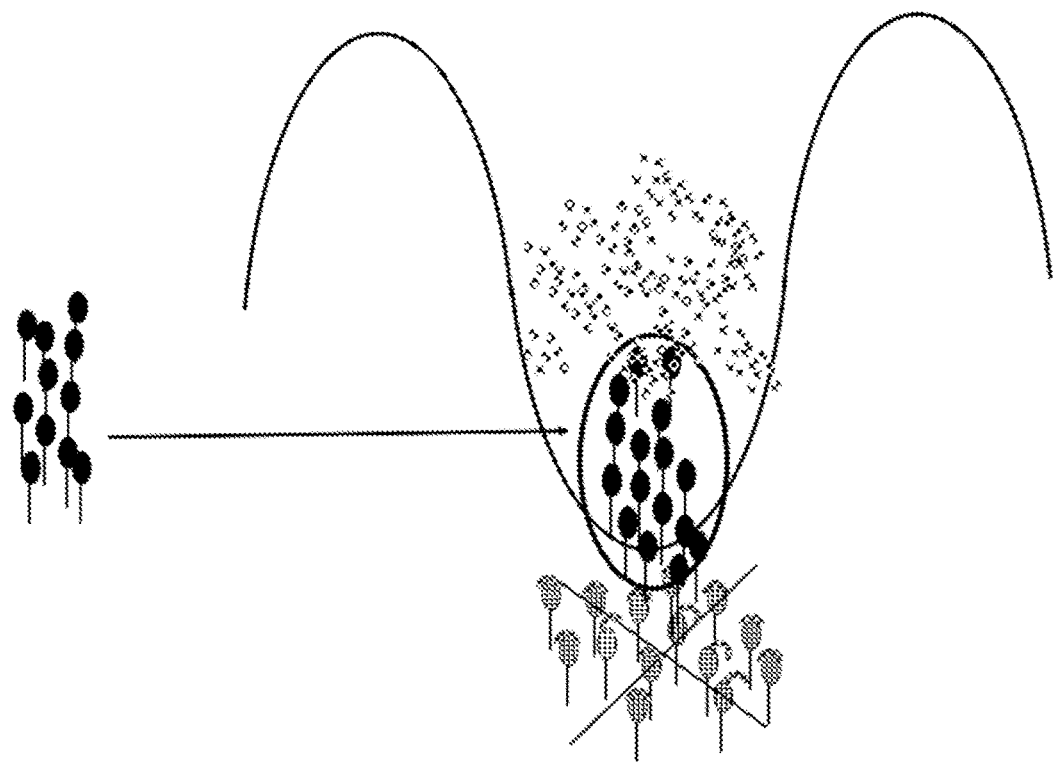
Figure 3F:
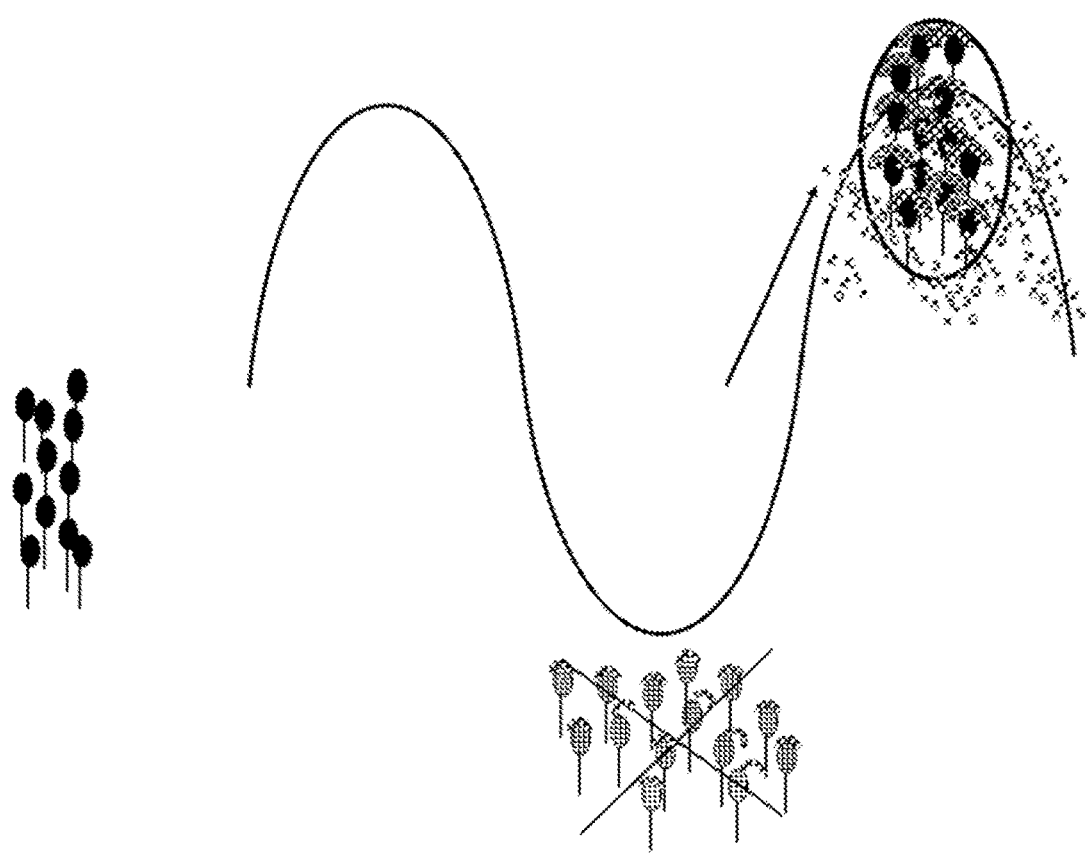

For each aliquot, mix (can use Vortexer) for about 2 seconds and incubate for about 20 minutes. After about 20 minutes, wash with buffer and centrifuge for about 30 seconds. Remove as much of the supernatant as possible without disturbing the pellet. Add more buffer (usually about 200 ul but may be less if sperm count was low), resuspend pellet and vortex for about 5 seconds. Place on cytometer SIP tube. Run the sample on the cytometer on SLOW (slow and fast are based on BD accuri c6 cytometer settings), this will record data points on a C6 file or score in some way. FIGS. 2A(1)-2F(2) show data from a cytometer for one assay of one ejaculate. The figures on the right show cytometer images and corresponding figures on the left show the graph of % sperm Fc receptor positive versus time as obtained from the cytometer readings. This ejaculate cycled rapidly, producing 2 minima of FcR positivity over the assay interval and should have high fertility if the female is healthy.

The inventors have discovered that there is a relationship between expression of markers on sperm over time and the fertility quality of the sperm for the ART procedure. Using the information about this relationship, particularly the number of cycles of appearance of a peak or a maxima marker expression relative to a baseline or minimum, e.g., by monitoring the expression of an Fc receptor on the sperm head, the fertility quality can be determined or diagnosed. This FcR expression relationship is relatively constant between individual samples from the same species incubated or held under the same conditions and between individual samples. The time relationship can be established for use in any sample of the same species/strain of animal, based on the establishment of the time relationship in a prior semen sample. Moreover, the correlation between cycles of FcR expression maxima and fertility quality can be applied to semen samples from an individual at a later time point. As such, the assay as described herein allows one to diagnose and predict the time point of optimum sperm fertility quality from future samples, e.g., samples acquired within about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, 33, 34, 35, 36, 37, 38, 39, 40, 41, 42, 43, 44, 45, 46, 47 38, 39, 50 hours or more from the first. In certain embodiments, the samples can be compared after from about 1 hr to about 30 days, from about 1 day to about 30 days, from about 1 day to about 29 days, from about 1 day to about 28 days, from about 1 day to about 27 days, from about 1 day to about 26 days, from about 1 day to about 25 days, from about 1 day to about 24 days, from about 1 day to about 23 days, from about 1 day to about 22 days, from about 1 day to about 21 days, from about 1 day to about 20 days, from about 1 day to about 19 days, from about 1 day to about 18 days, from about 1 day to about 17 days, from about 1 day to about 16 days, from about 1 day to about 15 days, from about 1 day to about 14 days, from about 1 day to about 13 days, from about 1 day to about 12 days, from about 1 day to about 11 days, from about 1 day to about 10 days from about 1 day to about 9 days from about 1 day to about 8 days, from about 1 day to about 7 days, from about 1 day to about 6 days, from about 1 day to about 5 days, from about 1 day to about 4 days, from about 1 day to about 3 days, from about 1 day to about 2 days after the first.

Diagnosing Sperm Having Suitable Fertility Quality

In certain aspects, the disclosure provides a method for time-based monitoring of one or more markers related to fertility stage, capacitation state or maturation stage of sperm in a semen sample to determine the fertility quality of semen. Preferably the marker is a lectin or an Fc receptor or another biological marker that can be correlated to the Fc receptor.

Specifically, the fertility quality of sperm depends on the relationship of the time-based expression of the marker being monitored and the number of cycles of expression maxima of the marker relative to baseline or minima by cohorts of sperm in the semen. In IUI studies to date, the percent of pregnancies increased when sperm produced more cycles of expression maxima of the marker per unit time, that is, a higher cycling frequency. Indeed, when marker expression showed a high expression (i.e., a maxima) followed by decrease in marker expression (i.e., a minima) with no further increase in expression (i.e., no additional maxima), the pregnancy rate was 0%. Notably, this abnormal expression of absent cycling is not seen in ejaculates from bulls bred for fertility.

The monitoring of the obtained semen sample encompasses the following steps of:
  i. determining the percentage of sperm in the semen sample having a marker/indicator of its metabolic status during incubation post collection at various time points, thereby providing a time-based graph of the marker expression for that semen sample; and ii. determining the number of times that the marker cycles through expression maxima to diagnose fertility quality of the sperm.

Aliquots can be taken from the incubated semen sample at regular intervals beginning at the time at which the semen sample is first collected. In one embodiment aliquots are taken every 5 minutes, every 10 minutes, every 15 minutes, every 20 minutes or every 30 minutes. It is preferable to take and assay aliquots at the smallest reasonable time intervals, including continuous monitoring of attributes amenable to such and paralleling FcR expression, depending on the time it takes to conduct the assay or other form of monitoring. The smaller the time intervals between assaying of aliquots, the better the ability to process determine cycles of marker expression maxima.

Monitoring of semen samples can be performed by any means known to those skilled in the art. A preferred method for monitoring is by use of a cytometer. (See FIGS. 2A(1)-2F(2)).

It should be noted that the semen sample can be ejaculate, sperm retrieved from the male reproductive tract such as needle aspirated sperm, or washed semen. In accord with the present invention, to produce pregnancy, the sperm must be actively cycling between marker expression maxima and minima. In certain embodiments, the marker is a sperm Fc receptor or sperm lectin.

Accordingly, in an aspect, the present description provides methods capable of determining the quality of sperm in an ejaculate to provide increased fertility in the form of pregnancy results. The methods described herein involve monitoring, in real time, changes in the metabolic status of sperm in a specific semen sample. In certain embodiments, the methods provide a means determining the potential fertility of semen for use in infertility clinics.

In an embodiment, the disclosure provides a method for diagnosing ejaculate fertility potential to obtain improved pregnancy results by a time-based assay of a semen sample from a male, the time-based assay method comprising the steps of:

i. providing a semen sample from a male, and incubating the sample under controlled conditions;

ii. selecting a marker or biomarker that is indicative of fertility quality of sperm, wherein expression of the biomarker changes with time;

iii. determining or detecting the level of expression of the marker or biomarker by sperm of the semen sample at a plurality of time points in an aliquot of the semen sample, wherein the fertility state, capacitative state, or maturation state of the sperm in the aliquot of the semen sample parallels that of the bulk semen sample;

iv. determining or detecting the number of times that the sperm in the aliquot of the semen sample express the marker or biomarker at a maxima, thereby determining the fertility quality of the sperm.

In certain embodiments, the method includes the step of processing or administering the sperm or another ejaculate from the same male. In certain embodiments, the sperm administered are those that proceed through at least two cycles of expression of the biomarker at a maxima or a minima or both.

In certain embodiments, the method includes a step of processing or administering the sperm that proceed through at least two cycles of expression of the marker or biomarker at a maxima (and/or a minima). In certain embodiments, wherein the sperm do not cycle through at least two marker or biomarker expression maxima (and/or minima), the method includes the step of administering an agent or modifying culture conditions to facilitate or enhance the maturation state or capacitation state of the sperm, and optionally administering the sperm to a female or to an oocyte.

In an additional aspect, the disclosure provides a method for diagnosing ejaculate fertility quality to obtain improved pregnancy results by a time-based assay of a semen sample from a male, the time-based assay method comprising the steps of:

a. creating akinetic model, wherein creating said kinetic model includes:

i. providing a semen sample from a male, and incubating the sample under controlled conditions;

ii. selecting a marker or biomarker that is indicative of fertilization quality of sperm, wherein expression or amount of the biomarker changes with time;

iii. determining or detecting the level or amount of expression of the marker or biomarker in an aliquot of sperm from the semen sample at a plurality of time points to provide a kinetic model of sperm maturational state based on the level or amount of expression of the at least one marker or biomarker, wherein the state of the sperm in the aliquot of the semen sample parallels that of the (bulk) semen sample;

iv. determining or detecting the number of times that the sperm in the aliquot of the semen sample express the marker or biomarker at a maxima (and/or a minima), thereby determining the fertility quality of the sperm in the semen sample (or in a subsequent semen sample from the same male); and b. providing a semen sample to be tested, and detecting for expression of the at least one biomarker as performed in (a), and calibrating the at least one biomarker expression displayed by the semen sample to said kinetic model of biomarker expression from step (a) to correlate the at least one biomarker expression during sperm maturation or capacitation and gain of or enhanced fertility;

c. calculating a time for freezing or preparing said semen sample or freezing or preparing a subsequent sample from the same male for use in insemination from the calibration, wherein at said time the sperm are optimized for fertilization quality for the procedure to be used, for example IUI; and d. processing or administering said semen sample or a subsequent sample (i.e., test sample) from the same male to an egg, a female, or combination thereof by an in vitro fertilization or artificial insemination method, e.g., IUI or IVF at about said time point of step (c), thereby optimizing said enhanced fertility of said semen sample or subsequent semen sample from the same male upon insemination of said semen sample.

In any of the aspects or embodiments, the methods include the step of treating said semen sample with at least one of a chemical agent that modulates the rate of sperm maturation or capacitation, an environmental stimulus that modulates the rate of maturation or capacitation, or an atmospheric condition that modulates the rate of maturation or capacitation.

The assay can be conducted on an aliquot of semen or an aliquot of washed sperm in a synthetic medium which, if desirable, allows one to assay sperm in wash medium and follow sperm that produce cohorts of sperm that move through the sperm fertility cycle in the wash medium to determine the time for insemination and whether pregnancy is possible. In any aspect or embodiment, the method can include a step of assessing the level of the biomarker by a detectable label which binds the biomarker or the ligand either directly or indirectly.

In any aspect or embodiment, the semen sample is from a mammal. In any of the aspects or embodiments, the mammal is e.g., a human, cow, horse, cow, pig, dog, sheep, or goat.

In any aspect or embodiment, the methods further comprise a step of freezing said semen sample or vitrification of said semen sample.

In any aspect or embodiment, wherein the kinetic model of biomarker expression during sperm capacitation comprises a sperm biomarker which binds to the constant region of an antibody.

In any aspect or embodiment, wherein the semen sample is not treated by fixation.

In any aspect or embodiment, the kinetic model of biomarker expression during sperm capacitation comprises more than one biomarker.

In any aspect or embodiment, the first of said plurality of time points is obtained immediately after collection of said semen sample.

In any aspect or embodiment, the kinetic model of biomarker expression during sperm capacitation is developed using ejaculates from the same species of the second semen sample.

In any aspect or embodiment, the methods include a step of administering an agent or an environmental stimulus to modulate maturation or rate of capacitation. In any aspect or embodiment, the agent is at least one of an endocannibinoid, bicarbonate 8-butyryl cAMP or combination thereof. In any aspect or embodiment, the environmental stimulus is selected from the group consisting of barometric pressure, atmospheric condition or pressure, temperature change and agitation. In any aspect or embodiment, the atmospheric condition comprises a gas which is selected from the group consisting of a nitric oxide, ozone, argon, cyanide and CO2. In any aspect or embodiment, the CO2 concentration is greater than 5%.

In any aspect or embodiment, the marker or biomarker is a lipid selected from the group of phosphatidyl serine, phosphatidlycholine, phosphatidyl ethanolamine and sphingomyelin. In any aspect or embodiment, the intracellular marker or biomarker is selected from the group consisting of: intracellular pH, intracellular concentration of HCO3, intracellular concentration of fragmented DNA, mitochondrial Calcium and intracellular concentration of Calcium. In any aspect or embodiment, the marker or biomarker binds a glycoprotein or an anionic polysaccharide. In any aspect or embodiment, the marker or biomarker binds a glycosaminoglycan, a sulfated glycosaminoglycan, a sulfated glycan and a sulfated polylactosaminoglycans. In any aspect or embodiment, the marker or biomarker is selected from the group consisting of heparin, fucoidan, ZP3, a glycoprotein or fragment thereof derived from the egg vestments, and a Lewis antigen. In any aspect or embodiment, the marker or biomarker is a physiologic activity selected from the group consisting of percent of sperm displaying motility, motility grade, frequency of beating of flagella of said sperm cell, ability of said sperm cell to penetrate mucus, loss of adhesion of said sperm cell, hypoosmotic swelling of said sperm cell, chemotaxis, thermotaxis and metabolic status of said sperm cell. In any aspect or embodiment, the biomarker comprises a molecule secreted or expelled by said sperm cell.

In any aspect or embodiment, the marker or biomarker comprises the appearance of exocytic vesicles or hybrid vesicles in solution. In any aspect or embodiment, the secreted or expelled molecule is selected from the group consisting of an enzyme, a proenzyme, an agent, a reactive oxygen species, an exosomal vesicle, a dye and DNA fragments. In any aspect or embodiment, the secreted or expelled agent is selected from the group consisting of an antibody bound fluorophore, a fluorophore and an enzyme. In any aspect or embodiment, the marker or biomarker is selected from the group consisting of Fertility-associated antigen, soybean trypsin inhibitor, an Fc receptor and CD46.

In any aspect or embodiment, freezing said semen sample comprises adding a cryoprotectant selected from the group consisting of trehalose, glycerol, propylene glycol, dimethylsulfoxide, sucrose and egg yolk.

In another aspect of this embodiment, the semen sample is assayed for said marker at intervals ranging from 1, 2, 3, 4, 5, 10, 12, 15, 20, 25, 30 minutes or more, which can depend on the rate of change of expression of the marker, on the time required to perform the assay, etc. In a further aspect, the assay preferably utilizes an aliquot of the semen sample or an aliquot of sperm producing results correlated to the sperm in the dose.

In certain embodiments, step (iii) includes determining or detecting the level of expression of the biomarker for a predetermined amount of time, e.g., about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180 minutes or more. In certain additional embodiments, step (iv) of the method includes determining or detecting the number of times the sperm in the aliquot of the semen sample express the biomarker at a maximum or peak within the predetermined time of (iii).

In another aspect of the invention, the predetermined period of time for assaying the semen is set to allow time to detect at least two cycles of expression of the biomarker, wherein a cycle includes a maximum followed by a minimum and increasing expression to a following maximum. In certain embodiments, the predetermined time period for the method is about 2.5 hours.

In certain embodiments, the maxima is a biomarker expression level that is greater than about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150% or more as compared to baseline or a minima. In certain embodiments, the maxima is a biomarker expression level that is greater than about 1 fold, 2 fold, 3 fold, 4 fold, 5 fold, 6 fold, 7 fold, 8 fold, 9 fold, 10 fold, 15 fold, 20 fold, 25 fold, 30 fold, 35 fold, 40 fold, 45 fold, 50 fold, 55 fold, 60 fold, 65 fold, 70 fold, 75 fold, 80 fold, 85 fold, 90 fold, 95 fold, 100 fold, 150 fold, 200 fold, 250 fold, 300 fold, 350 fold, 400 fold, 450 fold, 500 fold, 750 fold, 1000 fold, 2000 fold or more as compared to baseline or a minima.

In certain embodiments, the minima is a biomarker expression level that is the same or less than baseline or is below a peak or maxima expression level by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. In certain embodiments, the minima is a biomarker expression level that is the same or less than baseline or is below a peak or maxima expression level by about 1 fold, 2 fold, 3 fold, 4 fold, 5 fold, 6 fold, 7 fold, 8 fold, 9 fold, 10 fold, 15 fold, 20 fold, 25 fold, 30 fold, 35 fold, 40 fold, 45 fold, 50 fold, 55 fold, 60 fold, 65 fold, 70 fold, 75 fold, 80 fold, 85 fold, 90 fold, 95 fold, 100 fold or more, including all values in between.

If the assay shows the sperm having a maxima of expression followed by a minimum and no increase in expression toward a following maximum, the semen in that ejaculate is unlikely to provide fertility when inseminated into a female.

In another aspect of this embodiment, the biomarker is selected from, though not limited to fertility-associated antigen, soybean trypsin inhibitor, a ligand, a lectin, an enzyme, or a receptor, which is expressed on the surface of the sperm, or internally or both. In one embodiment, a ligand includes, but preferably is not limited to, a protein, a glycoprotein, a carbohydrate, a glycolipid, or a lipid, including ones detected by relative membrane fluidity rather than lipid molecular structure, as reflected for example in relaxation times of fluorescence polarization measurements, to distinguish different membrane regions, such as lipid rafts. In another embodiment the biomarker is selected from, though preferably not limited to, acrosome length, acrosome morphology, acrosome ruffling, expression of a cell surface molecule, electrostatic charge of said sperm, permeability of sperm membrane, a lipid, cholesterol, phosphatidylserine, a sugar, a protein, an intracellular ion, and bicarbonate.

In certain embodiments, the biomarker is a molecule present on the surface of the sperm or that is shed by the sperm into the medium surrounding the sperm, for example, a sperm Fc receptor (FcR), CD46, a carbohydrate, glycoprotein, carbohydrate binding protein, proteoglycan, glycolipid, a lipid, or a lectin). As long as the marker used can be correlated to sperm fertilization ability, it can be used in accord with the present invention. In certain embodiments, the biomarker is a sperm Fc receptor on the surface of the sperm head. In certain embodiments, the biomarker is a sperm FcR, wherein the FcR is indicative of a fertility state of the sperm.

In another embodiment, there is a method for determining or diagnosing the fertility quality of a semen sample for insemination in a female by monitoring a change in the metabolic status of sperm in the semen sample during incubation, the method comprising the steps of:
  i. selecting a marker that is indicative of a fertility status of sperm, wherein expression of the marker changes during said incubation,
  ii. determining the level of expression of the marker by sperm of the semen sample at a plurality of time points during said incubation, wherein an aliquot of said sample is assayed at each time point, and
  iii. determining the number of times during said predetermined period that said level of expression of said marker goes through a level of expression corresponding to a maximum level of Fc expression of the sperm followed by said marker going through a level of expression corresponding to a minimum level of FcR expression of the sperm, thereby determining the fertility quality of the semen sample for insemination to provide improved pregnancy results In a preferred embodiment, a method for diagnosing the fertility quality of newly collected semen ejaculate for obtaining improved positive pregnancy results comprises the steps of:
  i. collecting a semen ejaculate,
  ii. removing a small portion of the collected semen for assaying aliquots of sperm of said ejaculate over time for expression of a Fc receptor marker indicative of a fertility stage of said sperm,
  iii. determining the number of times the marker passes through a maximum of expression,
  iv. thereby determining the fertility quality of said semen for insemination of a female to obtain improved positive pregnancy results, and optionally processing or administering the sperm having an enhanced fertility quality.

In any aspect or embodiment, the sperm sample is incubated at a constant temperature during the determining or detecting (monitoring) of the biomarker for the metabolic status.

In one embodiment, binding of a first ligand evokes the appearance of a secondary biomarker, which is detected by contacting a secondary marker with a supplemental ligand. Alternatively, assays in accord with the present invention can be conducted with agents that do not bind, but enter the sperm or interact in some other way (such as lipid insertion into one of the lipid bilayers on the sperm or entry into the sperm during fusion events between the acrosomal and plasma membrane to produce pores) to provoke a change with time that can be monitored, preferably for a visible change.

In another nonlimiting aspect of this embodiment, the permeability of a dye by said sperm or fragments thereof is assayed in an aliquot of said sperm sample by monitoring by the intensity of said dye in the sperm or fragments thereof. Sperm are known to bind seminal plasma agents onto the sperm membrane. It has now been found that sperm actually can imbibe agents from their surrounding medium. Therefore, fragments of sperm should be construed to include agents sperm acquire as cargo, not just sperm as formed in the testis or epididymis.

In another aspect of embodiments of the invention, the expression of a cell surface biomarker is monitored, and the time point selected to process the semen sample is determined with respect to an earlier time point when the sample maximally expresses the biomarker.

In another aspect of embodiments of the invention, the expression of a cell surface biomarker is monitored, and the time point selected to process the semen sample is determined with respect to the earlier time point when expression of said biomarker in said sample has decreased relative to a peak expression and subsequently begins to increase from a minimum in the expression.

In one embodiment, the described method is based on the percentage of sperm in the semen sample having a specified biomarker. In one aspect, the specified biomarker is a biochemical marker, which is optionally present on the cell surface. Regardless, the biomarker reflects or is indicative of the metabolic fertility status of the sperm. In certain embodiments, the marker is not limited to a sperm specific marker.

In another aspect, the description provides a method for determining the percentage of sperm in the semen sample having the biomarker that reflects the metabolic fertility status of the sperm. The assay comprises the steps of a) removing an aliquot from the semen sample; b) contacting the aliquot with a first ligand to said biomarker; c) detecting binding of said ligand by said sperm; and d) determining the percentage of sperm in said aliquot which binds the ligand. In an alternative aspect of this embodiment, step d) can be replaced by the step of assessing the level of the biomarker by a detectable label which binds the biomarker or the ligand either directly or indirectly.

In another aspect the description provides a method of determining the concentration of said biomarker detected in sperm of said semen sample comprising: a) removing an aliquot from the semen sample; b) contacting the aliquot with a first ligand to said biomarker; c) detecting binding of said ligand by said sperm; and d) determining the amount of biomarker expressed by sperm in said aliquot by quantitating the binding of the biomarker by the ligand; thereby determining the concentration of said biomarker detected in sperm of said semen sample.

In any of the aspects or embodiments described herein, the ligand is labeled with a detectable label, preferably a visible label. In any of the aspects or embodiments described herein, detecting the binding of the ligand by the sperm includes detecting label bound directly or indirectly to the sperm, or fragments of the sperm. In any of the aspects or embodiments described herein, a sperm fragment is either associated or disassociated from intact sperm. In any of the aspects or embodiments described herein, detecting the binding of the ligand by the sperm encompasses contacting the sperm in the aliquot with a second ligand which binds to the first ligand. In any of the aspects or embodiments described herein, the first ligand and/or the second ligand is an antibody. In any of the aspects or embodiments described herein, the antibody can be either polyclonal or monoclonal antibodies, and can comprise one or more labels.

Markers of Metabolic Status

Optimal sperm fertility can be defined on the basis of numerous attributes such as number of viable sperm, sperm motility (both the percentage that are motile and the type of motility exhibited), sperm morphology, acrosomal integrity, etc. It is known that all sperm go through a series of metabolic changes once ejaculation has occurred and the sperm is mixed with plasma from the seminal vesicles and with other fluids. The sperm "maturation" which includes "capacitation" that follows ejaculation is necessary for sperm to achieve fertilizing ability. A number of membrane changes are associated with these processes (Bearer, 1990). However, Applicant has found that the Fc receptor provides a preferred marker for fertility state. Thus, any biological marker that can be correlated to the Fc receptor is useful in the practice of the present invention.

EXAMPLES

Example 1

Fc Receptor Assay

The assay is performed directly on 10 µl aliquots of raw semen, thawed washed semen in synthetic medium or washed semen in synthetic medium. A larger amount of raw semen may be used for oligozoospermic samples, however, the preferred method of cell counting for oligozoospermic samples, where possible, is to resuspend the cells in a smaller buffer volume for cytometric analysis, as low as 100 µl, and to collect events on what corresponds to the fastest flow rate on an BD Accuri c6 cytometer. Semen is collected into a collection cup.

Before running this assay, be sure (1) that semen is collected and incubated as described in Working Example 1 to minimize process failures and (2) that assay reagents are at ambient temperature before use (22-26° C.). GREEN 1, RED 2 and BLUE 3 are discussed above.

1. Prepare Assay Mixture (not Premixed)
   i. Into 1.5 ml tube, pipet the following IMMEDIATELY before use and in the order directed below.
   ii. 100 µl GREEN 1
   iii. 20 µl RED 2
   iv. 10 µl neat semen
   v. 5 µl BLUE 3, mix.
   vi. You will repeat this assay at 30 min intervals, but ideally 15 min intervals. Keep reagents at ambient at all times during assay run.
2. PREPARE ASSAY MIXTURE (Pre-mixed and pre-aliquotted reagents)
   i. Into 1.5 ml tube, pipet the following IMMEDIATELY before use and in the order directed below.
   ii. 120 µl GREEN 1/RED 2 mixture (mixed 5:1 v/v)
   iii. 10 µl neat semen
   iv. 5 µl BLUE 3, mix.
   v. You will repeat this assay at 30 min intervals, but ideally 15 min intervals. Keep reagents at ambient at all times during assay run.
3. Incubate
   a. Incubate tube for 20 minutes at ambient temperature. (A 15 minute incubation is possible but the risk of artifact increases if the assay is shortened excessively.)
4. Wash
   a. Add 1 ml BUFFER at ambient temperature (PBS buffer (8 g NaCl; 0.2 g KCl; 1.44 g $Na_2HPO_4 \cdot 7H2O$; 0.24 g $KH_2PO_4$; $H_2O$ to 1 liter. PH 7.2 or PBS buffer tablet without calcium without magnesium as sold by MP Biomedicals and reconstituted according to manufacturer's instructions as described previously)
   b. Microfuge 30 seconds at 2000×g (about 6,000 rpm in microfuge).
   c. Carefully remove supernatant with 1 ml pipette. Leave small amount of fluid to avoid disturbing pellet.
5. Score
   a. Add ~300 ul BUFFER to cell pellet and mix gently to resuspend. Resuspension volume for scoring is related to sperm concentration: oligozoospermic samples require smaller resuspension volumes, as low as 100 µl, or counting times will be lengthened to analyze the required number of events. Where cell number is low, it is preferred to first increase flow rate on the cytometer. If this permits acquisition of 5,000 events within about 60 seconds, it is preferable. If sperm counts are too low to enable this, volume reduction at resuspension is needed.
   b. Place tube containing resuspended cells onto cytometer SIP tube and analyze on a calibrated cytometer using the "Cytometer Scoring" template (see Cytometer Scoring SOP for further details).
6. Analyze Diagnostic Results and Determine Fertility Quality Diagnostic Analysis
   a. FcR initial status—(NOTE: this diagnostic can be run ONLY when a coagulated sample is tested immediately post-collection. Liquified samples may have normal cohorts already maturing, resulting in scores that are high but nonetheless normal.) Determine the percentage of positive sperm at the first time point. If it exceeds 35%, the collection shows abnormal premature deployment of FcR. This is associated with infertility in livestock IUI and raises the index of suspicion for human male-factor infertility.
   b. FcR kinetics-plot FcR % positive against time. See FIGS. 2A(1)-2F(2). Normal kinetics over a 2.5 h period involve maturation of more than one cohort of sperm, with usual periodicity of 1.5-2 h, although some collections show cohorts maturing at shorter intervals. In humans, cattle and pigs, swim up yield, a known fertility marker in cattle IUI, is maximal 1 hr after peak FcR positivity, making FcR kinetics a predictive assay. Ejaculates showing only a single peak of maturation by FcR have been found in some cases to also have other abnormalities. Single cohort ejaculates are not seen in fertility-selected livestock. These results and initial human data raise the index of suspicion that single-cohort ejaculates have male-factor issues in pre-ART (IUI, timed intercourse with female fertility drugs) that could compromise pregnancy outcome.

c. Improving freezing damage resistance—it is known that increasing fluidity of membranes correlates with improved freezability. Methods as described herein, measure FcR receptor expression, which can be reflective of membrane changes resulting in increased fluidity. As such, the described methods can be used to enhance viability of samples that are to be frozen, by allowing freezing at a state that minimizes the cell damage than occurs upon thawing. As sperm processing conditions for freezing differ between laboratories, it is best for each laboratory to calibrate the sperm state that is best, when combined with their specific process, at improving post-thaw viability. This can be done by running the assay and processing/freezing aliquots at the start of each assay time point. The sperm state, identified by assay, that produces the highest swim up yield or viability on post-thaw analysis is the state most suitable for dose freezing by the procedures in that specific laboratory.

Treatment with State-Adjusted Sperm for IUI a. Plot percentage of positive cells. The percentage of cells positive for the Fc receptor will usually begin to increase in the timeframe of 30 min-2.5 h post-collection for coagulated samples, and may already be elevated at first assay point for post-liquefaction samples with early-maturing cohorts, confounding interpretation of the first cohort peak. Time zero=time of assay inception.

b. Graph points, looking for an increase between two points of at least 30% for 30 min intervals. The increase between 3 points should be at least 30% when tested at 15 min intervals. When such an increase in positivity of cells is seen, wait 30 min and then immediately perform procedure of IUI insemination with the portion of the sample prepared for this purpose. The preferred window of time falls within 30-60 minutes, and processing time may necessitate insemination at 45 min. Where possible, however, it is preferred that sperm be introduced into the uterus by IUI at a time when their expression of FcR is falling and reaching a minimum, as opposed to passing the minimum and climbing.

See FIGS. 2A(1)-2F(2) for an actual sample example. Note that smaller increases in % positive FcR may still be associated with favorable outcomes, but are not preferred for sperm fertility state adjustment.

FIGS. 2A(1)-2F(2) show an example for identification of FcR peak and desired IUI time. Figure designated "C" draws attention to an increase in the population of FcR positive sperm—which often precedes the state of decrease and then the minimum itself—from which timing of sperm IUI should occur. Thus, Figure C is an example of the plot that would signify to the clinic that the critical sperm state is being approached and then attained. This is important because the clinic will not see the entire curve during sperm preparation, only the region necessary to adjust sperm state to a IUI-compatible state.

Cytometer Scoring

Before scoring this assay, be sure that semen is collected and incubated exactly as set forth above and that the assay is run exactly as described above, to minimize process failures.

Start Equipment
 i. Turn on computer
 ii. Turn on cytometer (Accuri, Lansing, MI now made by BD)
 iii. If needed, empty waste bottle and fill sheath bottle with DI water Open Template and Name File
 a. Click Assay 1 Template
 b. Select File>Save CFlow file as . . .
 c. Name file by date by typing date code under File Name
 d. Click Save Collect Data
 a. Under the red Collect tab, click on desired cytometer grid (1A is for first sample, first donor, 1B is for second sample, first donor. 2A is for first sample, second donor, etc.)
 b. Next to cytometer grid (e.g., A01) type sample information and assay time (time when collection is assayed)
 c. Check that stoplight shows green color. Load sample onto SIP tube on cytometer and pull out plastic tube support underneath tube
 d. Click Run
 e. After data are acquired, adjust gate on density plot so that the percentage of positive sperm (the population on the right) can be determined. Record this number. This involves first gating sperm with a cell gated if desired (useful for human samples, not required for cattle samples). To analyze cells in the cell gate for FcR positivity, as in plots shown, this involves placing a quad gate as shown, above the most positive edge of the negative pool by assay fluorescence in channel 1, and determining the percentage of FcR positive sperm in the upper right quadrant. As the lower quadrants are not used in this assay, a vertical gate may also be used. Remove sample from SIP tube
 f. For the next sample, repeat process above starting with step 3a
 g. After the samples for that assay time are finished, click Backflush, wait for stoplight to show green, then click Unclog Clean and Shut Down Equipment
 a. Between every sample, place towel under SIP, select Backflush or Unclog
 b. At the end of the day, place a tube of cleaning fluid on the cytometer, select well H1 and click Run. Run for 2 minutes. Then place a tube of water on the cytometer, select well H2 and click Run. Run for 2 minutes. Allow water to clean system for at least 2 minutes.
 c. Turn off cytometer, then turn off computer
 d. Follow all instructions for operation, cleaning and preventive maintenance as detailed in the manufacturer's instrument manual.

Example 2

Diagnostic: Assay Cycling Rate Correlates to Pregnancy Rate

Figures 4A, 4B, 4C:
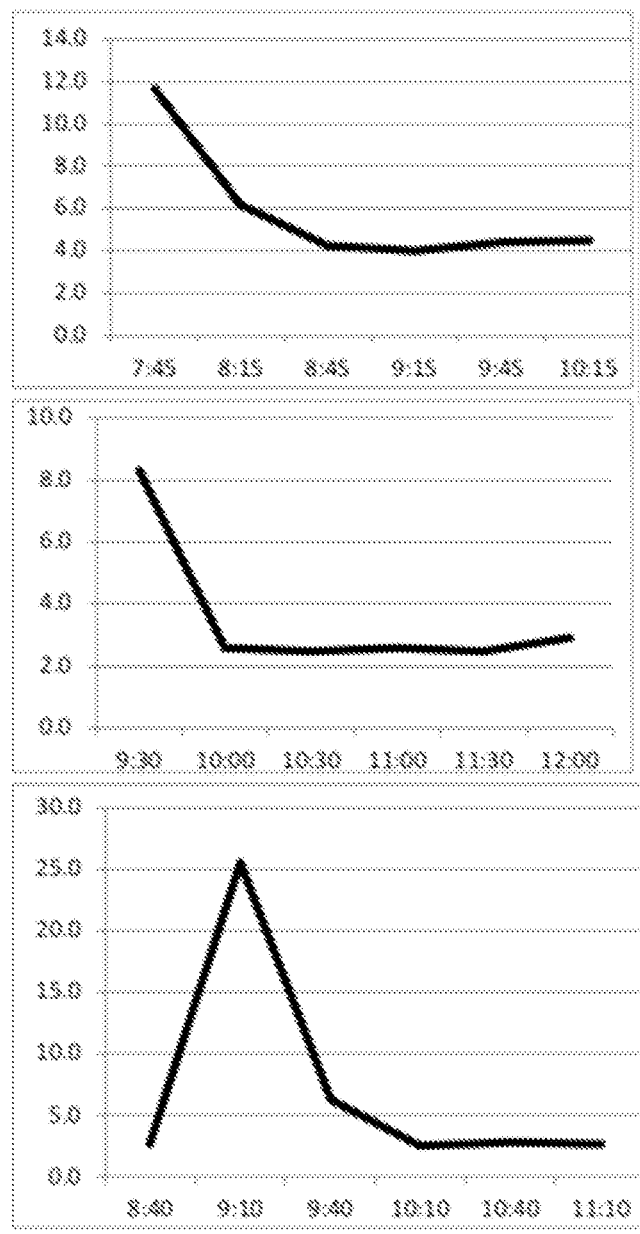
FIG. 4A-4I illustrate groups of sperm having different cycling rates as assayed in accord with the present invention.
Figures 4D, 4E, 4F:
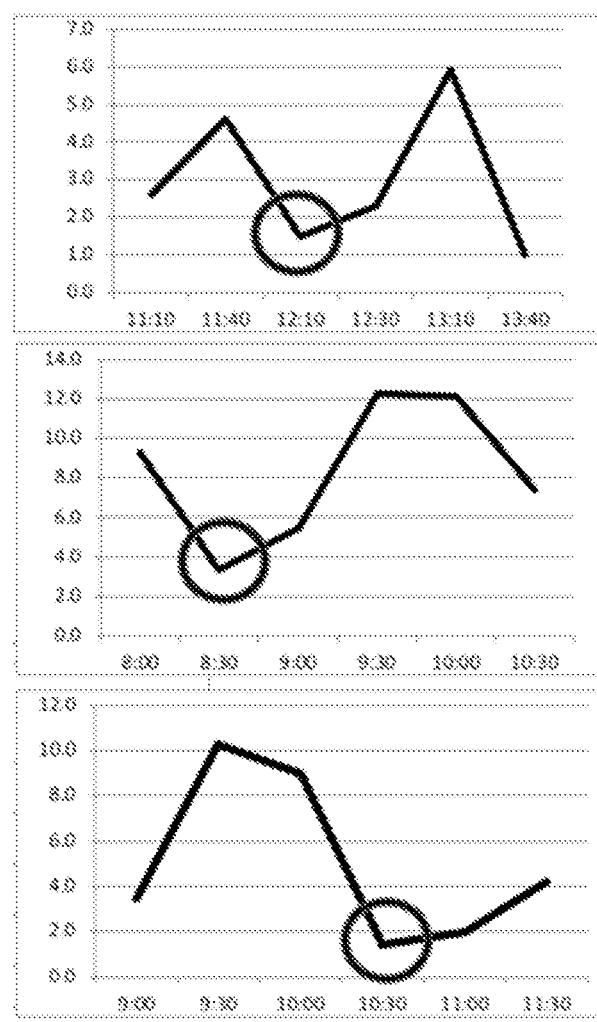
Figures 4G, 4H, 4I:
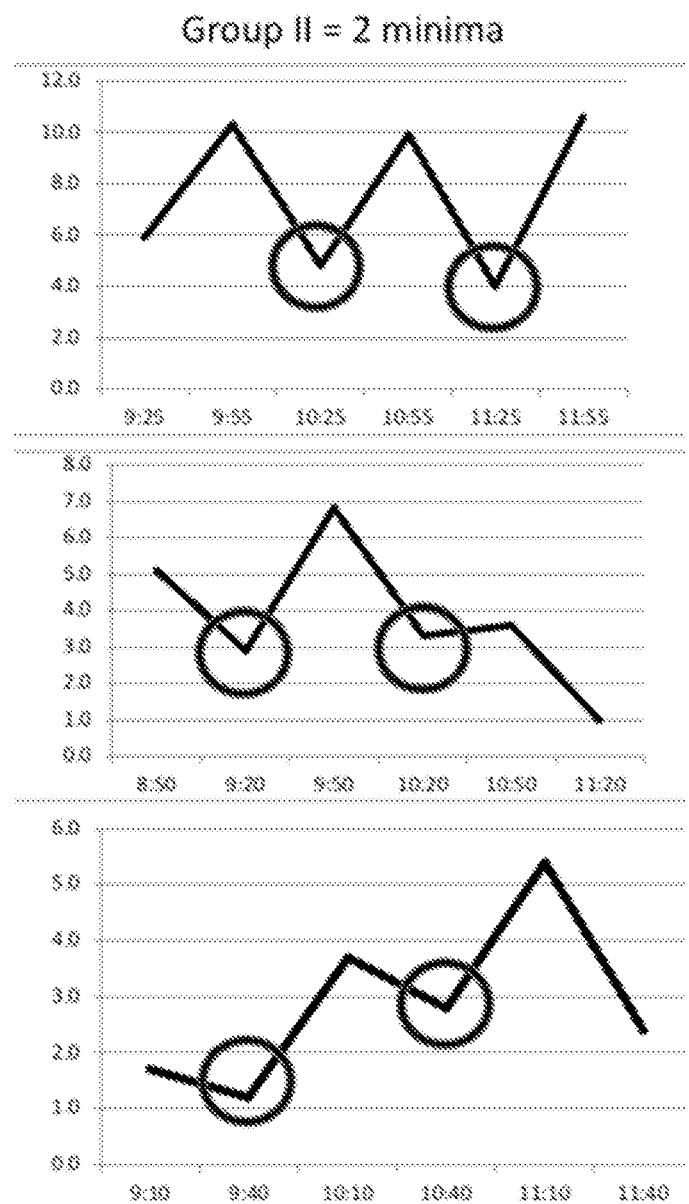

Semen samples were assayed as described in Example 1 above. Graphs are neat semen assays from ejaculates, showing % Kinetix positive on Y axis and time on X-axis. Group I has no minimum; Group II has one (1) minimum; Group III has two (2) minima. FIG. 4 shows examples of the assay graphs for these groups running over a 2.5 hour period showing minima for IUI insemination times (circled). The following table shows the relationship of cycle frequency with pregnancy rate in accord with the present invention. Relationship of Ejaculate Cycling Rate and IUI Pregnancy Achievement

| Ejaculate Group | Ejaculate Cycling Rate (#Minima/2.5 h) | Ejaculate Pregnancy Rate |
|---|---|---|
| I | 0-no cycling | 0% (n = 3 ejaculates) |
| II | 1-slow cycling | 14% (n = 14 ejaculates) |
| III | 2-fast cycling | 31% (n = 13 ejaculates) |

This data illustrates use of cycling for diagnostic purpose, for example, by cryobanks or by IUI clinics who want the couple back again if the first ejaculate produces no assay minimum, or one minimum when they may want to try for a 2-min ejaculate the next day, within the same ovulatory cycle. IUI procedures 24*h* apart are practiced at the discretion of the clinicians in the clinic from which data was collected. Thus, in any aspect or embodiment described herein, the methods include detecting at least one marker expression minima, e.g., a sperm FcR expression minima.

Thus, clinics and cryobanks can use the described methods not just as manufacturing process control to make semen doses for IUI that are of uniform sperm state but more simply as a diagnostic because it can identify men capable of producing IUI pregnancy with their partners, plus how likely the inseminating ejaculate or one produced close in time to the inseminating ejaculate will be to produce IUI pregnancy, versus men who should be fast-tracked directly to IVF due to male-factor infertility incompatible with IUI pregnancy achievement by the partner. Fast-cycling ejaculates will be more fertile in IUL. If a male patient produces a Group I or Group II ejaculate, a physician may wish to call the couple back to process another ejaculate 24*h* later, so that chances of pregnancy achievement are increased (when first ejaculate was suboptimal). A cryobank may desire to sell at a premium rapid cycling ejaculates for IUI—and reject men who consistently fall into the Ejaculate Group I noncyclers or sell that semen for IVF/ICSI only. Ejaculates cycling at average rate could be preferentially routed to other forms of assisted reproduction than IUI or sold at standard price for IUL. The diagnostic assay of the present invention can be run on collected sperm prior to freezing or on previously frozen sperm when thawed.

The methods as described herein can be run exactly as disclosed in Example 1 above, on sperm in neat semen, on sperm in extender diluent (for freezing), or washed sperm. Exact processes currently in use at clinic or cryobank would be used for processing the semen for IUI or storage. The only change would be to identify an ejaculate's cycling rate to determine sperm dose IUI quality or to determine likelihood of producing pregnancy and patient stratification into single IUI or repeat IUI procedures. As described in other sections for real-time sperm state adjustment, if a sperm bank freezes doses at a uniform specific state (instead of at random more or less useful states as is currently the practice), the bank can also distribute to customers a precise downstream procedure to insure sperm so processed are inseminated into the uterus at the state compatible with IUI pregnancy.

A real time assay of the metabolic status of sperm in the specific semen sample allows a better, more consistent determination of the potential fertility of ejaculates and washed sperm for use in a clinic or for sale from a cryobank. The real time monitoring of the metabolic status of sperm in a semen sample as it progresses through its individual metabolic rate of sperm activation, for example, can be used to determine the real time occurrence of expression of the fertility trait in the individual semen sample, so as to assess the potential fertility of the semen. Advantageously, the methods disclosed herein can be used to increase positive pregnancy results and render the assisted reproductive process more economical, simpler, safer and faster than current practices.

It has been found that a preferred marker of fertility state is an Fc receptor (FcR) on the head of sperm. The percentage of sperm in the population expressing Fc receptors on the head of sperm can be monitored over time to provide a plot of Fc receptor expression vs. time. The expression of Fc receptors can be monitored by use of a labeled ligand that binds to the Fc receptor. Useful such ligands include labeled antibodies having no other affinity for the sperm. The plot of Fc receptor expression vs. time shows the potential in an ejaculate to produce a cycle of a maturing population (cohort) of sperm expressing then shedding Fc receptors to reach a maximum and declining to a minimum followed by a second population (cohort) of sperm expressing Fc to reach a maximum followed by declining to a minimum and, then, possibly even a third population (cohort) of sperm expressing Fc to reach a maximum followed by declining, and possibly cycling of even more cohorts from the reserve pool of sperm that diminishes with each cycle. See FIGS. 3A-3F.

Example 3

Figures 5A, 5B:
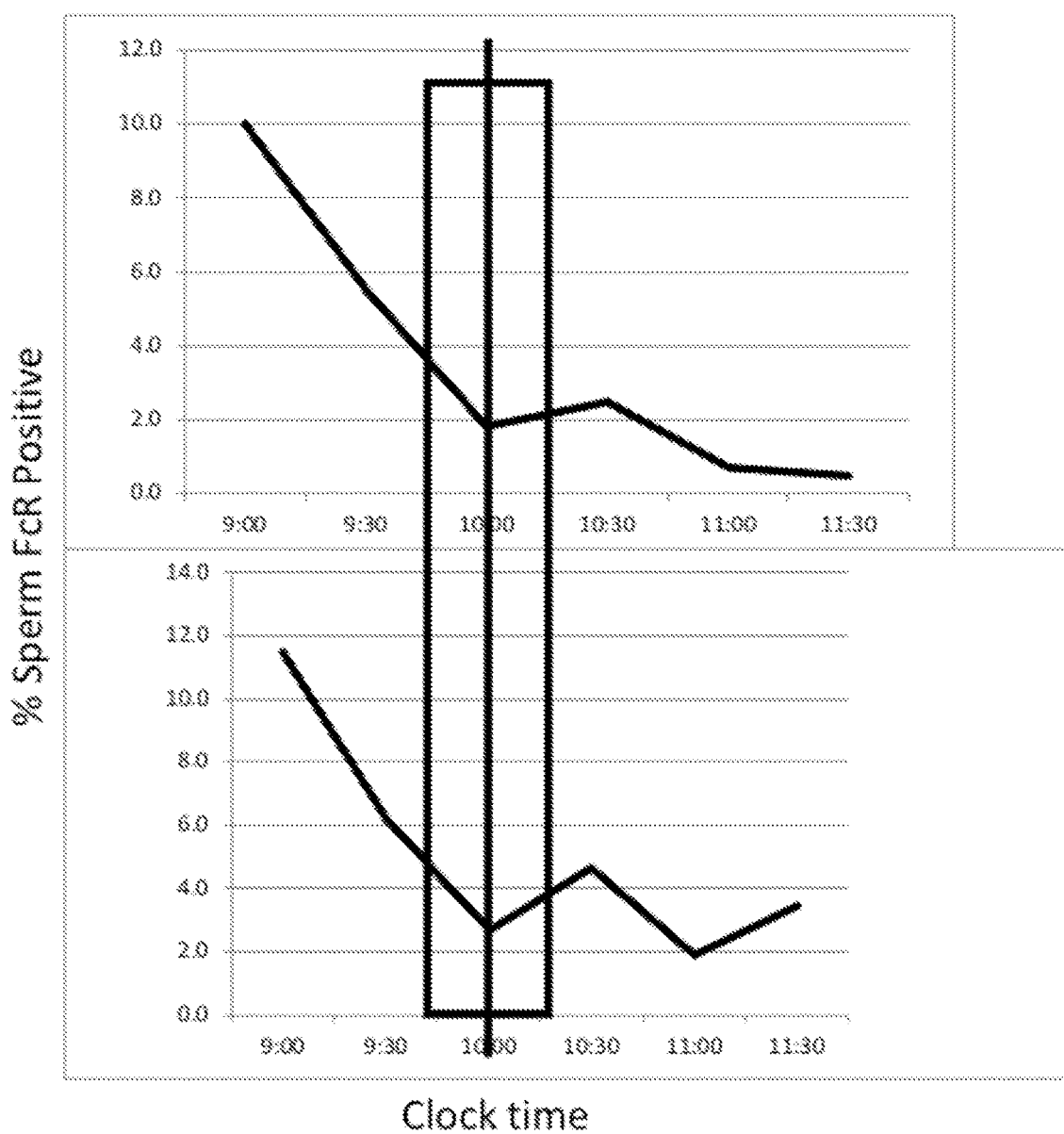
FIG. 5A-5J illustrate cycle kinetics are similar within the same donor is seen in ejaculates produced 24*h* apart (FIG. 5A-5H) but not one month apart (FIG. 5I-5J).
Figures 5C, 5D:
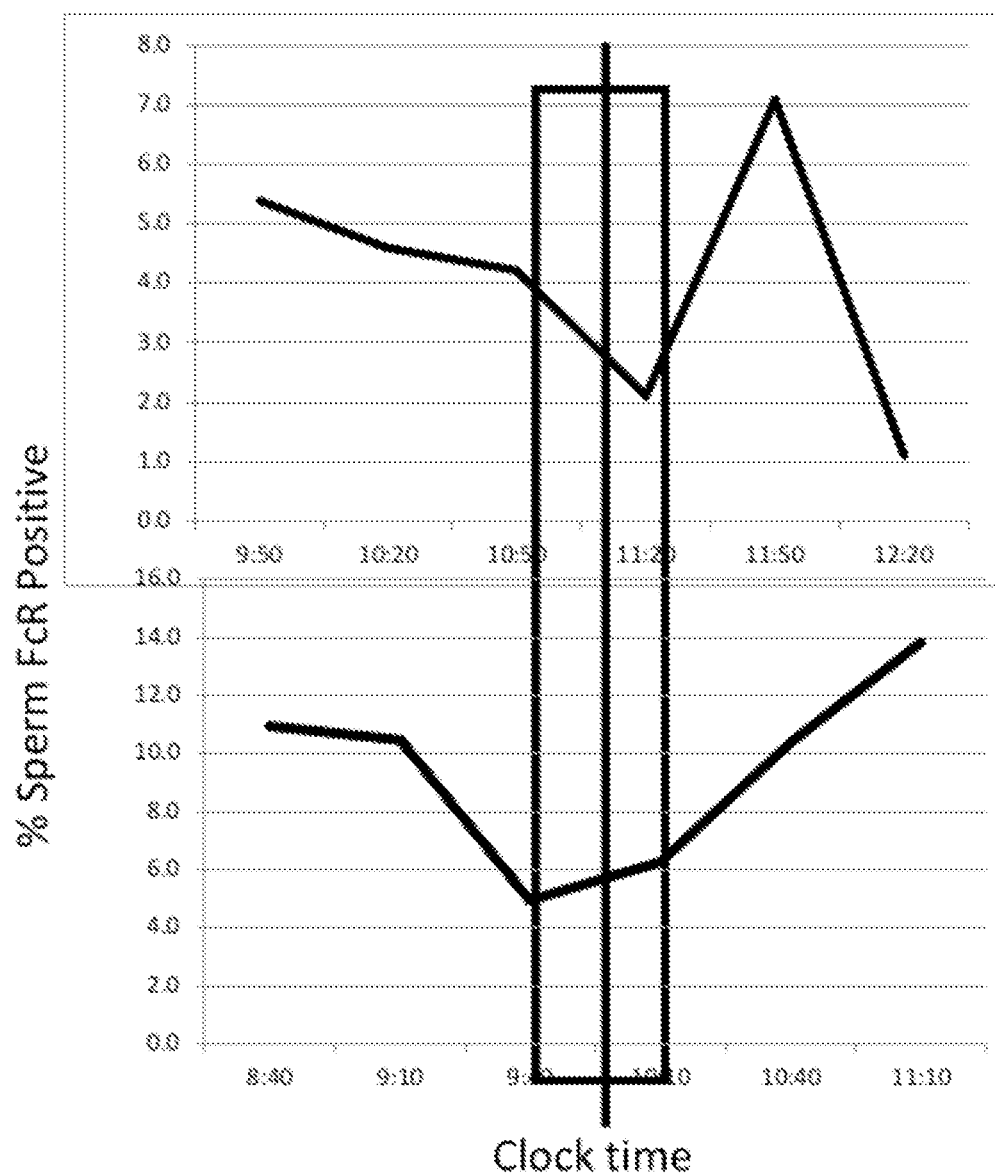
Figures 5E, 5F:
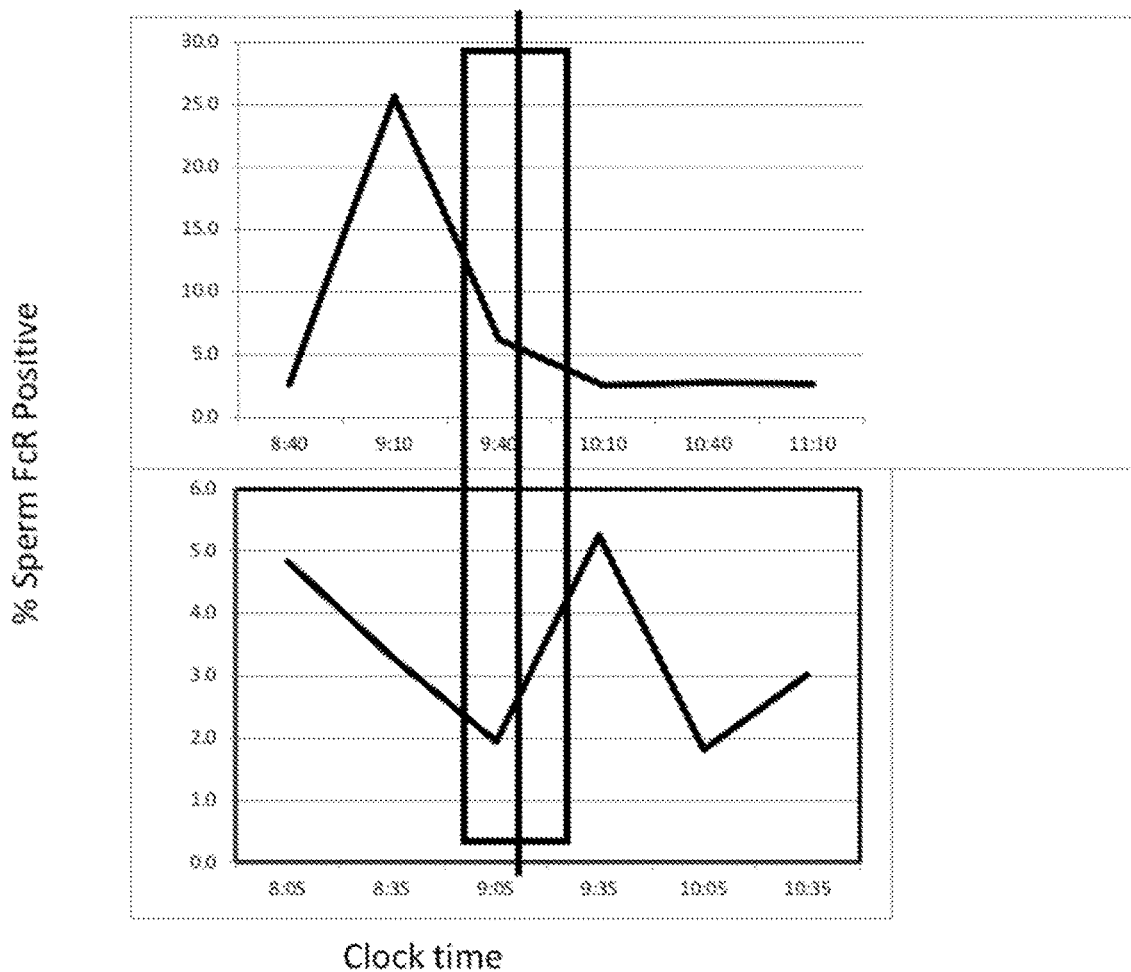
Figures 5G, 5H:
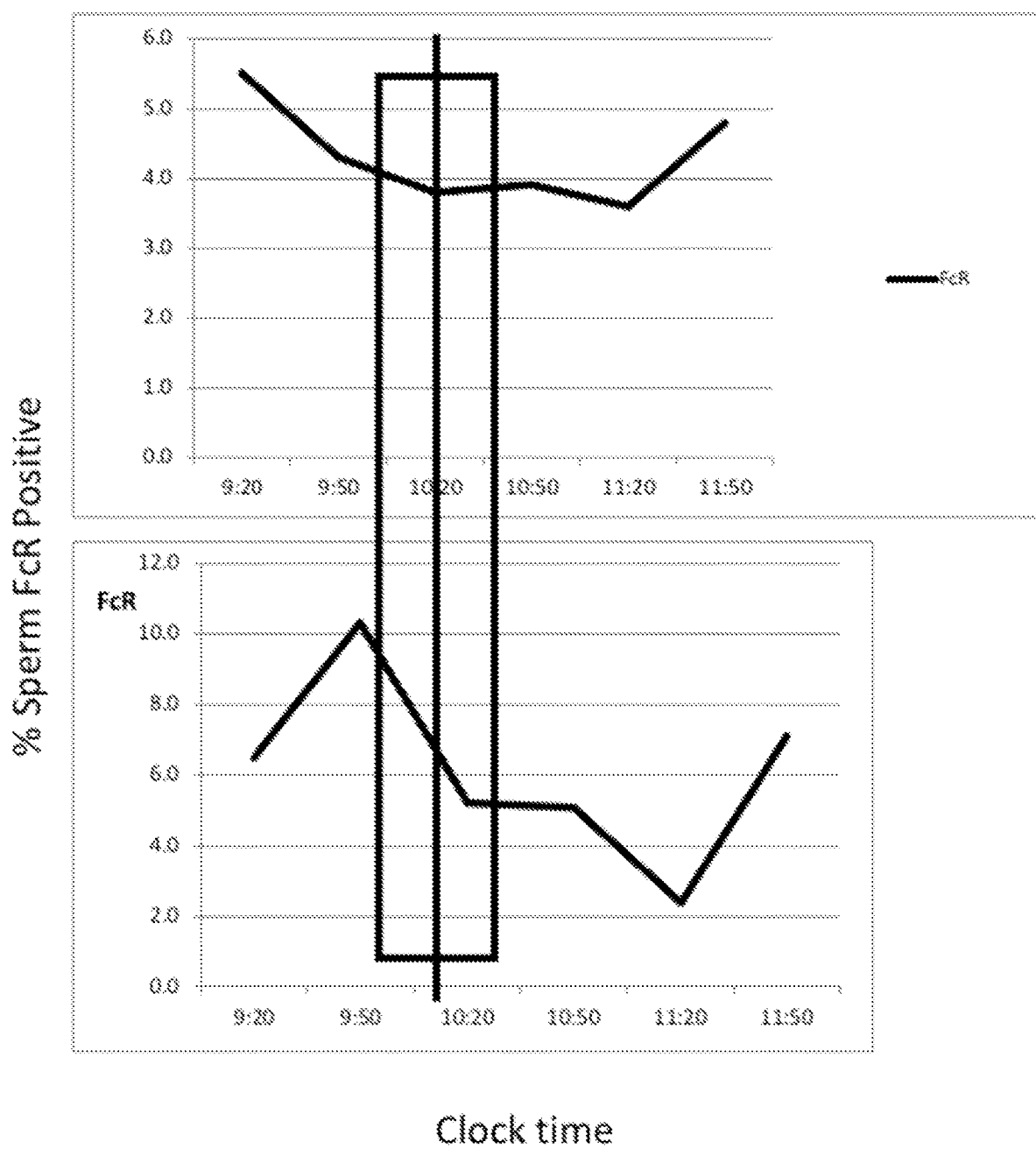
Figures 5I, 5J:
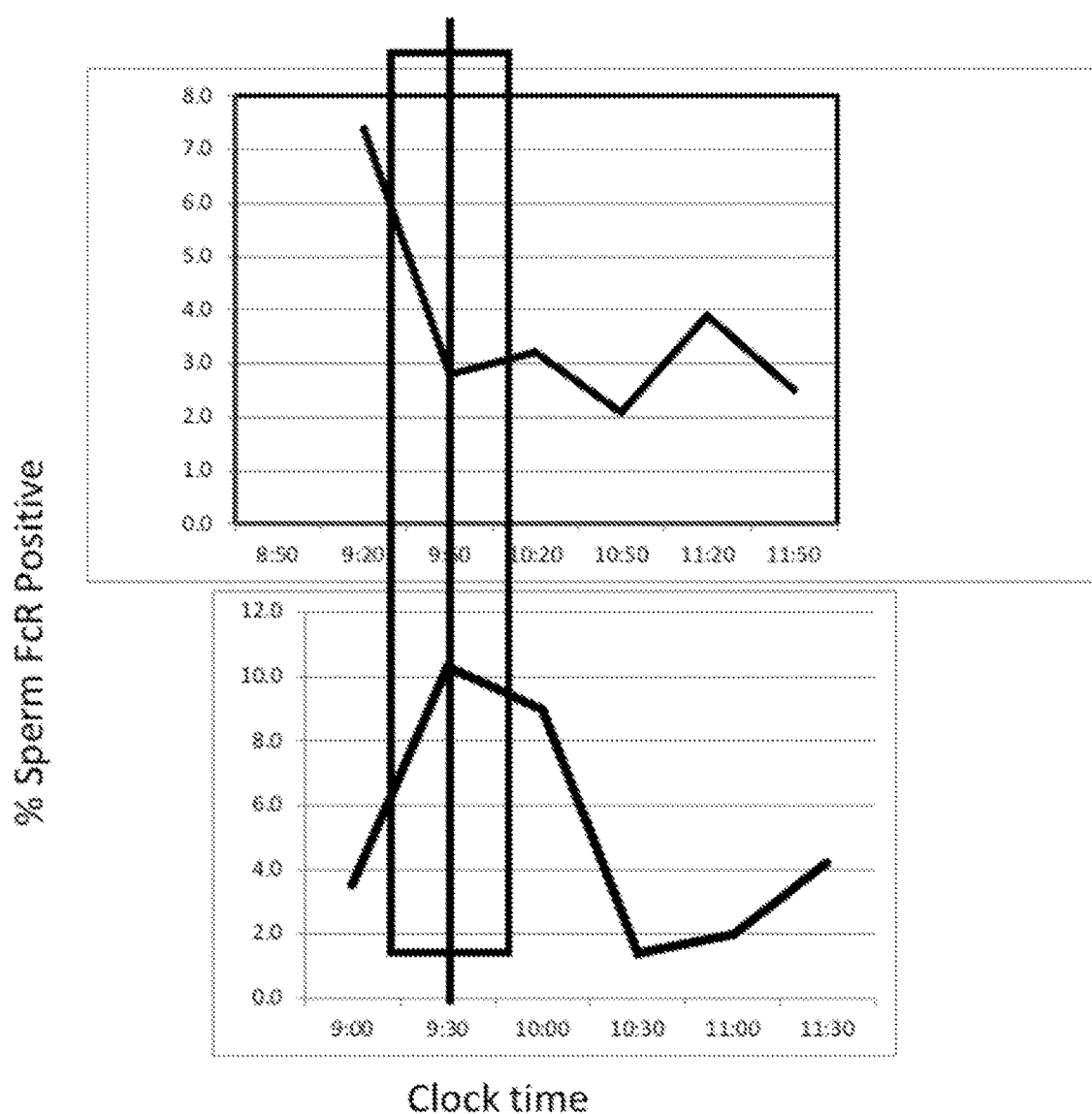

Similarity of cycle kinetics within the same donor is seen in ejaculates produced 24*h* apart (FIG. 5A-5H) but not one month apart (FIG. 5I-5J).

It is useful to use the methods as described herein to predict not only with an ejaculate, but between ejaculates from the same male. As shown in FIG. 5, assays run on ejaculates produced on successive days by different males are similar within the same male but not between males. FIGS. 5A-5B, 5C-5D, 5E-5F, and 5G-5H represent results from different donors taken 24 hours apart (day 1 is top graph, day 2 is bottom graph). Thus, it is possible to predict the FcR minimum of the second ejaculate from the first ejaculate. Patient one (FIG. 5A-5B) is a precise match, Patients 2 (FIG. 5C-5D) and 3 (FIG. 5E-5F, and 5G-5H) produce ejaculates with the FcR minima within 30 min of each other on successive days, which could enable successful prediction of sperm state from the first day's ejaculate to enable pregnancy from the second ejaculate even if the second ejaculate is not assayed. Patient 3 in another pair of ejaculates on successive days also produced a pair of ejaculates in which one did not cycle, which would indicate a need for a different treatment approach in patient workup. The last male, Patient 4 (FIG. 5I-5J), produced single samples one month apart and these lacked similarity of timing of the first FcR minimum.

Prediction from one day's ejaculate to the next for optimal state of the second ejaculate to produce IUI pregnancy has utility. It has the potential to simplify clinical work and cost while still increasing the probability of pregnancy, although not to the degree seen with more intensive assay of the inseminate ejaculate. With these data, however, a patient could produce a specimen at a site for assay and then visit the clinic the next day to produce the specimen used for insemination.

In accord with the described methods, to diagnose the fertility quality of an ejaculate, semen is collected for diagnosis, an aliquot is taken for time-based assaying at periodic intervals and the assay profile is used to diagnose or determine fertility quality of the semen. In accord with the present invention, number of cohorts of sperm expressing Fc receptors in cycles of a maxima and declining to a minima in the assay profile correlates to the fertility quality of the semen. In studies, when the assay initially shows expression Fc receptor at a maxima followed by decline and no further cycles of cohorts of semen showing increased expression (or successive minima) of Fc receptors, the sperm have little to no likelihood of providing fertility for IUI insemination, and may not provide fertility in IVF but may require IVF/ICSI and may fail in that approach. If the assay shows additional cohorts of sperm increasing to a maxima and declining (or cycles of minima), the semen has better fertility quality correlating with the number of cycles of cohorts of sperm reaching further maximums and declining, especially within a given time period (rate of cohort cycling per unit time, frequency of sperm cycling).

Those skilled in the art may assay for and monitor other markers that correlate to fertility, for example, motility, acrosome length or morphology, appearance of the acrosomal membrane or components thereof, which appear in a punctate pattern visible through fenestrations in the plasma membrane, such pattern starting at the acrosomal rostrum and extending further down the head, expression of a cell surface molecule of sperm of the semen sample, electrostatic charge of sperm of the semen sample, and permeability of a dye by sperm or fragments thereof of sperm of the semen sample or of sperm-derived agents (such as FcR) shed into the medium surrounding the sperm. As long as the time-based assay correlates to FcR expression of sperm or shedding thereof, increased rates of pregnancy can be expected to result.

All patents, patent applications, and published references cited herein are hereby incorporated by reference in their entirety. The disclosure set forth herein has been particularly shown and described with references to preferred embodiments thereof, it will be understood by those skilled in the art that various changes in form and details may be made therein without departing from the scope encompassed by the appended claims.

REFERENCES

Ahlgren, M., Bostrom, K., Malmqvist, R. (1975), "Sperm transport and survival in women with special reference to the Fallopian tube", *The Biology of Spermatozoa* (eds. Hafez, E. S. E., and Thibault, C. G.), pp 63-73, Karger Medical and Scientific Publishers.

Agarwal, A., Mulgund, A., Hamada, A., and Chyatte, M. R. (2015) "A unique view on male infertility around the globe." Reprod. Biol. Endocrinol. 13: 37. DOI 10.1186/s12958-015-0032-1.

Alukal, J. P. and Lipshultz, L. I. (2008), "Safety of assisted reproduction, assessed by risk of abnormalities in children born after use of in vitro fertilization techniques", *Nature Clin. Practice* 5(3): 140-150.

Barratt, C., Mansell, S., Beaton, C., Tardif, S., and Oxenham, S. (2011) "Diagnostic tools in male infertility—the question of sperm dysfunction." Asian Journal of Andrology, 13: 53-58. Bearer and Friend (1990) *J Elecon Micros Tech.* 16: 281-297.

Cohen-Dayag, A., Tur-Kaspa, I., Dor, J., Mashiach, S. and Eisenback, M. (1995) Sperm capacitation in humans is transient and correlates with chemotactic responsiveness to follicular factors. *Proc. Natl. Acad. Sci.* 92: 11039-11043

Fischer, B., and Bavister, B. D. (1993), "Oxygen tension in the oviduct and uterus of rhesus monkeys, hamsters and rabbits", *J. Reprod. and Fert.* 99: 673-679.

Guthrie, H. D., and Welch, G. R. (2012), "Effects of reactive oxygen species on sperm function", *Theriogenology* 78(8): 1700-1708.

Kobayashi, H., Hiura, H., John, R., Sato, A., Otsu, E., Kobayashi, N., Suzuki, R., Suzuke, F., Hyashi, C., Utsonomiya, T., Yaegashi, N., and Arima, T., (2009), "DNA methylation errors at imprinted loci after assisted conception originate in the parental sperm", Eur. J. Human Genet. 17: 1582-1591.

Moskovtsev, S. I., A. Qu, B. A. Cohen, R. A. Parkinson, J. Y. Zhang, A. Lee and C. L. Librach. (2017) "Preventing Fertility Failure in IUI with Kinetix Sperm Fe Receptor Test." Massachusetts Life Sciences Innovation Day (Boston, MA USA).

The invention claimed is:

1. A method for diagnosing ejaculate fertilization potential to obtain improved pregnancy results, the method comprising the steps of:
   i. providing a semen sample from a male, and incubating at least a portion of the sample under controlled conditions;
   ii. selecting a biomarker that is indicative of fertility quality of sperm, wherein the expression level of the biomarker changes with time;
   iii. detecting the expression level of biomarker by sperm of the semen sample at a plurality of time points in an aliquot of the semen sample, wherein the fertility state, capacitative state, or maturation state of the sperm in the aliquot parallels that of the semen sample;
   iv. detecting for a plurality of cycles that the sperm in the aliquot express the biomarker at a maxima relative to a baseline or a subsequent minima, wherein the presence of multiple cycles of maxima are indicative of sperm with enhanced fertilization potential, thereby determining the fertilization potential of the sperm; and
   v. processing the sperm from step (iv).

2. A method for enhancing fertilization potential of sperm in a semen sample from a male, the method comprising the steps of:
   a. creating a kinetic model, wherein creating the kinetic model includes:
      i. providing a semen sample from a male, and incubating at least a portion of the sample under controlled conditions;
      ii. selecting a biomarker that is indicative of fertilization potential of sperm in the semen sample, wherein the expression level or amount of the biomarker changes with time;
      iii. detecting the expression level or amount of the biomarker in an aliquot of sperm from the semen sample at a plurality of time points to provide a kinetic model of sperm maturational state based on the expression level or amount of the biomarker, wherein the maturational state of the sperm in the aliquot parallels that of sperm in the semen sample;

iv. detecting for a plurality of cycles that the sperm in the aliquot from the semen sample express the biomarker at a maxima relative to a baseline or subsequent minima, thereby determining the fertilization potential of the sperm in the semen sample, wherein the presence of multiple cycles of maxima or minima are indicative of sperm with enhanced fertilization potential, thereby determining the fertilization potential of the sperm; and b. providing a semen sample to be tested, and detecting for expression of the biomarker as performed in (a), and calibrating the biomarker expression level displayed by sperm in the semen sample to said kinetic model of biomarker expression from step (a) to correlate the biomarker expression during sperm maturation or capacitation with enhanced fertility;

c. calculating a time for freezing or preparing the semen sample or freezing or preparing a subsequent sample from the same male for use in insemination based on the calibration, wherein the sperm are optimized for fertilization potential; and d. processing or administering the sperm from the semen sample or a subsequent sample from the same male to an egg, a female, or combination thereof by an in vitro fertilization or artificial insemination method at about said time point of step (c), thereby optimizing the fertility potential of said the sperm in the semen sample or subsequent semen sample from the same male upon insemination.

3. The method of claim 1 or 2, wherein the biomarker is sperm Fc receptor.

4. The method of claim 1 or 2, wherein the method includes a step of processing or administering to a female or an oocyte the sperm that proceed through at least two cycles of expression of the marker or biomarker at a maxima (and/or a minima).

5. The method of claim 1 or 2, wherein the method further includes administering an agent or modifying a condition to facilitate or enhance the maturation state or capacitation state of the sperm.

6. The method of claim 1 or 2, wherein the semen sample is from a mammal.

7. The method of claim 6, wherein the mammal is a human, cow, horse, cow, pig, dog, sheep, or goat.

8. The method of claim 1 or 2, wherein the methods further comprise a step of freezing said semen sample or vitrification of said semen sample.

9. The method of claim 2, wherein the kinetic model of biomarker expression during sperm capacitation comprises a sperm biomarker which binds to the constant region of an antibody.

10. The method of claim 2, wherein the kinetic model of biomarker expression during sperm capacitation comprises more than one biomarker.

11. The method of claim 1 or 2, wherein the biomarker expression maxima is at least about 50% higher than a baseline or minima.

12. The method of claim 1 or 2, wherein the steps are performed using sperm selected from the group consisting of sperm in neat semen, sperm in extender, and washed sperm.

13. The method of claim 1 or 2, wherein the agent is at least one of an endocannibinoid, bicarbonate 8-butyryl cAMP or combination thereof.

14. The method of claim 1 or 2, wherein the method includes a step of administering to the sperm or to the semen an agent or environmental stimulus to modulate at least one of sperm maturation, capacitation, fertility quality or a combination thereof.

15. The method of claim 14, wherein the environmental stimulus is selected from the group consisting of barometric pressure, atmospheric condition or pressure, temperature change and agitation.

16. The method of claim 15, wherein the atmospheric condition comprises a gas which is selected from the group consisting of a nitric oxide, ozone, argon, cyanide and $CO_2$.

* * * * *